(12) United States Patent
Burke et al.

(10) Patent No.: US 11,517,540 B2
(45) Date of Patent: Dec. 6, 2022

(54) RESTORING PHYSIOLOGY IN IRON-DEFICIENT ORGANISMS USING SMALL MOLECULES

(71) Applicant: The Board of Trustees of the University of Illinois, Urbana, IL (US)

(72) Inventors: Martin D. Burke, Champaign, IL (US); Anthony S. Grillo, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/542,596

(22) PCT Filed: Jan. 11, 2016

(86) PCT No.: PCT/US2016/012855
§ 371 (c)(1),
(2) Date: Jul. 10, 2017

(87) PCT Pub. No.: WO2016/112381
PCT Pub. Date: Jul. 14, 2016

(65) Prior Publication Data
US 2018/0263926 A1 Sep. 20, 2018

Related U.S. Application Data

(60) Provisional application No. 62/251,964, filed on Nov. 6, 2015, provisional application No. 62/101,706, filed on Jan. 9, 2015.

(51) Int. Cl.
*A61K 31/122* (2006.01)
*A61P 7/06* (2006.01)
(Continued)

(52) U.S. Cl.
CPC .......... *A61K 31/122* (2013.01); *A61K 9/0019* (2013.01); *A61K 9/0053* (2013.01);
(Continued)

(58) Field of Classification Search
CPC ....... A61P 7/06; A61P 39/04; G01N 33/5008; G01N 2800/22
See application file for complete search history.

(56) References Cited

U.S. PATENT DOCUMENTS

2005/0163849 A1  7/2005  Wong et al.
2005/0176827 A1  8/2005  Lee et al.
(Continued)

FOREIGN PATENT DOCUMENTS

JP   2006/503076 A   1/2006
JP   2012/515725 A   7/2012
(Continued)

OTHER PUBLICATIONS

Aisen, Iron Metabolism, Current opinion in chemical biology, 3.2, 1999, pp. 200-206. (Year: 1999).*
(Continued)

*Primary Examiner* — Savitha M Rao
*Assistant Examiner* — Andrew P Lee
(74) *Attorney, Agent, or Firm* — Foley Hoag LLP

(57) ABSTRACT

Provided are methods of treating a disease or condition characterized by a deficiency of or a defect in an iron transporter using a small molecule. For example, the method may increase transepithelial iron transport, or it may increase iron release. Additionally, the small molecule may be hinokitiol, or it may be selected from the group consisting of amphotericin B, calcimycin, nonactin, deferiprone, purpurogallin, and maltol. Also provided is a method of iden- (Continued)

tifying a compound capable of treating a disease or condition characterized by a deficiency of or a defect in an iron transporter.

15 Claims, 23 Drawing Sheets

(51) Int. Cl.

| | |
|---|---|
| *A61P 39/04* | (2006.01) |
| *G01N 33/50* | (2006.01) |
| *A61K 45/06* | (2006.01) |
| *A61K 9/00* | (2006.01) |
| *A61K 31/34* | (2006.01) |
| *A61K 31/351* | (2006.01) |
| *A61K 31/4184* | (2006.01) |
| *A61K 31/4412* | (2006.01) |
| *A61K 31/7048* | (2006.01) |

(52) U.S. Cl.
CPC ............ *A61K 31/34* (2013.01); *A61K 31/351* (2013.01); *A61K 31/4184* (2013.01); *A61K 31/4412* (2013.01); *A61K 31/7048* (2013.01); *A61K 45/06* (2013.01); *A61P 7/06* (2018.01); *A61P 39/04* (2018.01); *G01N 33/5008* (2013.01); *G01N 2800/22* (2013.01)

(56) References Cited

U.S. PATENT DOCUMENTS

| | | |
|---|---|---|
| 2006/0128805 A1 | 6/2006 | Shah |
| 2012/0135091 A1 | 5/2012 | Roth et al. |

FOREIGN PATENT DOCUMENTS

| | | |
|---|---|---|
| JP | 2012/532128 A | 12/2012 |
| JP | 2014/503579 A | 2/2014 |
| WO | WO-2008/143869 A1 | 11/2008 |
| WO | WO-2009/138761 A1 | 11/2009 |
| WO | WO-2010/005851 A1 | 1/2010 |
| WO | WO-2013/054755 A1 | 4/2013 |
| WO | WO-2013/147214 A1 | 10/2013 |
| WO | WO-2014/152006 A2 | 9/2014 |

OTHER PUBLICATIONS

Garrick, A direct comparison of divalent metal-ion transporter (DMT1) and hinokitiol, a potential small molecule replacement, Biometals, 2019, 32, pp. 745-755 (Year: 2019).*
Extended European Search Report for EP Application No. 16735544.5 dated Jun. 21, 2018.
Gasche et al., "Ferric Maltol is Effective in Correcting Iron Deficiency Anemia in Patients with Inflammatory Bowel Disease: Results From a Phase-3 Clinical Trial Program," Inflammatory Bowel Diseases, 21(3): 579-588 (2014).
Ido et al., "Induction of Apoptosis by Hinokitiol, a Potent Iron Chelator, in Teratocarcinoma F9 Cells is Mediated Through the Activation of Caspase-3," Cell Prolif, 32(1): 63-73 (1999).
International Search Report and Written Opinion for International Application No. PCT/US 2016/012855 dated Apr. 8, 2016.
Written Opinion for International Application No. PCT/US2008/051486 dated Sep. 17, 2013.
Garrick et al., "Ferric-salicylaldehyde isonicotinoyl hydrazone, a synthetic iron chelate, alleviates defective iron utilization by reticulocytes of the belgrade rat," Journal of Cellular Physiology, 146:460-465 (1991).
Horvathova et al., "Erythropoietin-driven signaling ameliorates the survival defect of BMT1-mutant erthroid progenitors and eythroblasts," Haematologica, 97(10):1480-1488 (2012).
Search Report issued by the European Patent Office in corresponding Application No. EP 16735544.5, dated Dec. 12, 2019.
Veuthey et al., "Pathophysiology of the Belgrade rat," Frontiers in Pharmacology, 5(82):1-13 (2014).

* cited by examiner

RESTORING PHYSIOLOGY IN IRON-DEFICIENT ORGANISMS USING SMALL MOLECULES

RELATED APPLICATIONS

This application is the U.S. national phase of International Patent Application No. PCT/US2016/012855, filed Jan. 11, 2016; which claims the benefit of priority to U.S. Provisional Patent Application Ser. No. 62/101,706, filed Jan. 9, 2015; and U.S. Provisional Patent Application Ser. No. 62/251,964, filed Nov. 6, 2015.

GOVERNMENT SUPPORT

This invention was made with government support under Grant No. GM080436, awarded by the National Insititutes of Health. The government has certain rights in the invention.

BACKGROUND OF THE INVENTION

Iron is critical for numerous processes in all living organisms, but is toxic at high concentrations. Greater than twenty-five (25) human diseases arise from a deficiency of key iron transporters and regulatory proteins. Examples of such diseases include hypochromic, microcytic anemia caused by deficiencies of divalent metal transporter 1 (DMT1), hypochromic anemia caused by mitoferrin deficiencies, and hemochromatosis, which can be caused by decreased ferroportin levels. A common consequence of these deficiencies is thought to be the buildup of iron gradients across lipid membranes.

SUMMARY OF THE INVENTION

Small molecules, e.g., hinokitiol, restore physiology as measured by a restoration of growth in yeast deficient in the iron transporting complex Fet3Ftr1, as well as restore the transport of iron across monolayers of human Caco-2 epithelia deficient in DMT1. These studies support the untapped potential of treating iron deficiencies with small molecules, such as hinokitiol.

DETAILED DESCRIPTION OF THE INVENTION

Figure 1:
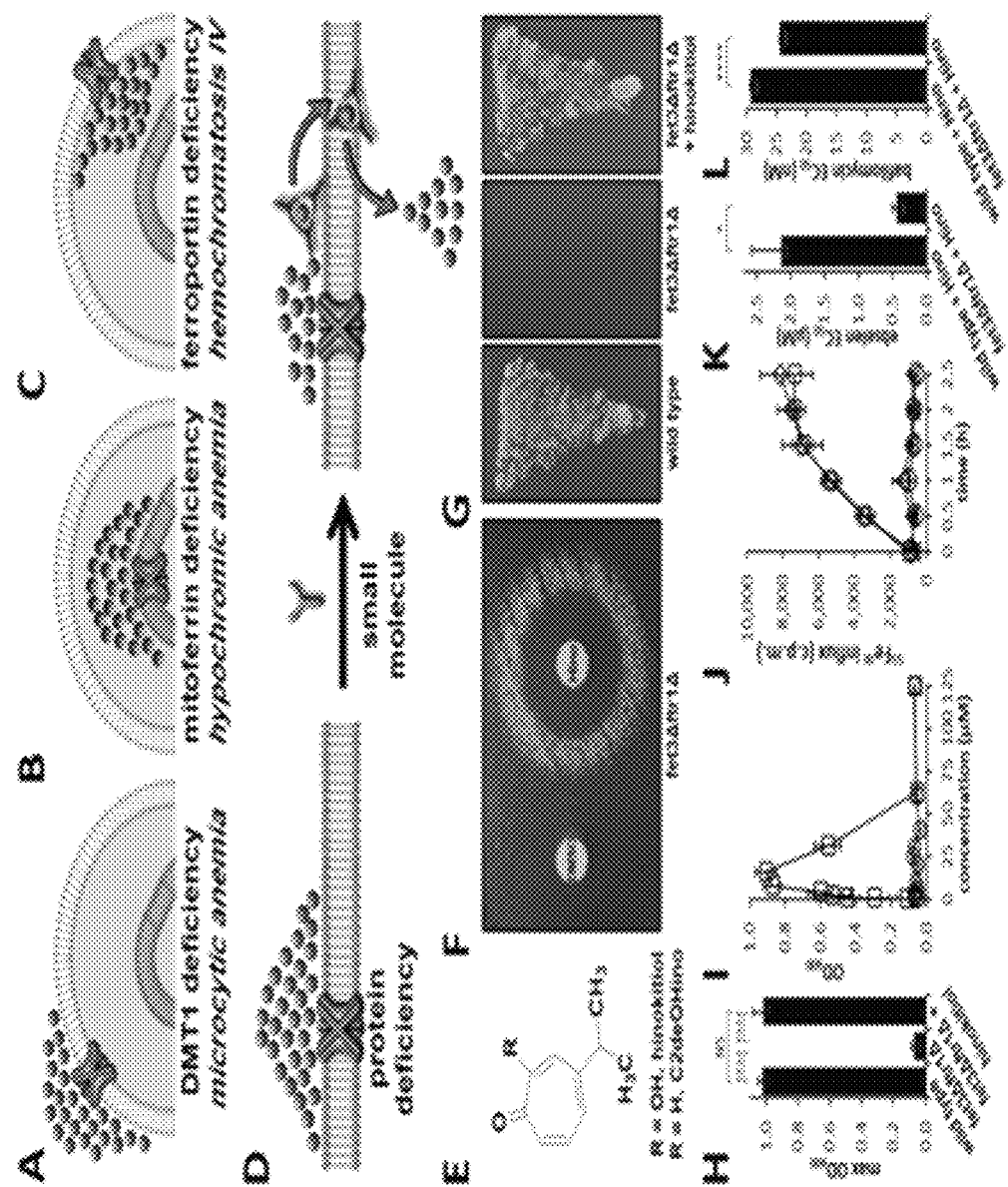
FIG. 1 illustrates the restoration of physiology to iron-deficient organisms with small molecules. Panel (A) is a simplified schematics of iron diseases related to improper influx; panel (B) illustrates the intracellular iron movement and panel (C) the efflux; panel (D) represents a small molecule iron transporter hypothesized to release formed iron gradients and restore physiology; panel (E) illustrates the structures of the small molecule natural product hinokitiol and C2deOHino; panel (F) shows that hinokitiol restores growth to yeast similar to wild type yeast on solid (panel (G)) and liquid media (panel (H)); panel (I) illustrates dose-dependent rescue of growth; panel (J) shows restoration of influx of $^{55}$Fe into cells; panels (K) and (L) illustrate that hino-rescued yeast are exceptionally sensitive to chemical inhibition of Pma 1 with ebselen and V-ATPase with bafilomycin, respectively.

The invention stems from the findings that small molecules, e.g., hinokitiol, restore physiology as measured by a restoration of growth in yeast deficient in the iron transporting complex Fet3Ftr1, as well as restore the transport of iron across monolayers of human Caco-2 epithelia deficient in DMT1. Hence the invention relates to the untapped potential of treating iron deficiencies with small molecules, such as hinokitiol.

As used herein, the term "treat" or "treatment" is defined as the application or administration of a compound, alone or in combination with a second compound, to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder). In the case of wound healing, a therapeutically effective amount is an amount that promotes healing of a wound.

As used herein, an amount of a compound effective to treat a disorder, or a "therapeutically effective amount" refers to an amount of the compound which is effective, upon single or multiple dose administration to a subject or a cell, in curing, alleviating, relieving or improving one or more symptoms of a disorder. In the case of wound healing, a therapeutically effective amount is an amount that promotes healing of a wound.

Administration "in combination with" one or more further therapeutic agents includes simultaneous (concurrent) and consecutive administration in any order.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic"

treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used in the present disclosure and claims, the singular forms "a," "an," and "the" include plural forms unless the context clearly dictates otherwise.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

As used herein, "subject" refers to a warm blooded animal such as a mammal, such as a human, or a human child, which is afflicted with, or has the potential to be afflicted with one or more diseases and disorders described herein.

For example, provided herein are methods of treating various disease or condition characterized by a deficiency of or a defect in an iron transporter in mammals (including humans and non-humans), comprising administering to a patient in need thereof a compound of the invention, or a pharmaceutically acceptable salt thereof. Such various disease or condition characterized by a deficiency of or a defect in an iron transporter include: hereditary hemochromatosis (which can also be accompanied by cirrhosis, cardiomyopathy, diabetes mellitus, polyarthropathy, hypogonadism), iron deficiency anemia, hypochromic microcytic anemia, anemia of chronic disease (resulting from, e.g., normochromic, normocytic anemia, chronic infections, ongoing inflammation conditions (e.g., inflammatory bowel diseases, vasculitides), autoimmune diseases, and neoplasia); iron overload (e.g., iron poisoning, chronic iron overload, ineffective erythropoiesis); fatigue, lethargy; dizziness; headaches; shortness of breath; ringing in ears; taste disturbances; restless leg syndrome; pallor; flattened; brittle nails (spoon nail); angular stomatitis (cracks at mouth corners); glossitis; blue sclera (whites of eyes); pale conjunctivae; pica (ice chewing); decreased maximum aerobic capacity; decreased athletic performance; lowered endurance; impaired temperature regulation; depressed immune function; increased rates of infection; impaired cognitive functioning and memory; compromised growth and development; and increased lead and cadmium absorption.

"Hinokitiol", as used herein, is represented by the structural formula:

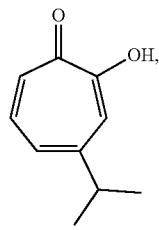

and is also referred to "β-thujaplicin", "2-hydroxy-6-propan-2-ylcyclohepta-2,4,6-trien-1-one" and "4-Isopropyl-tropolon".

One aspect of the invention relates to a method of treating a disease or condition characterized by a deficiency of or a defect in an iron transporter, comprising administering to a subject in need thereof a therapeutically effective amount of a small molecule, thereby treating the disease or condition characterized by a deficiency of or defect in an iron transporter.

In certain embodiments, the small molecule is selected from the group consisting of amphotericin B (AmB), calcimycin, nonactin, deferiprone, purpurogallin, and maltol, and any combination thereof.

In certain embodiments, the small molecule is selected from the group consisting of calcimycin, deferiprone, purpurogallin, and maltol, and any combination thereof.

In certain embodiments, the small molecule is hinokitiol.

In some embodiments, the small molecule is administered as a pharmaceutical composition.

The pharmaceutical compositions of the present invention can be administered in any number of ways for either local or systemic treatment Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

In certain embodiments, the small molecule is administered systemically. In certain embodiments, the small molecule is administered orally. In certain embodiments, the small molecule is administered intravenously.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituxin, PD4 inhibitors, p38 inhibitors, PDE4 inhibitors, and antihistamines. Additionally, iron supplements may be co-administered with a compound of the invention. In certain embodiments, the invention relates to co-administration of a compound of the invention, and deferiprone or another iron chelator therapy.

Thus, another aspect of the invention provides a pharmaceutical composition comprising a therapeutically effective amount of a compound of the invention and a second therapeutic agent selected from the group consisting of steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, acetylosalicylic acid, COX inhibitors, methotrexate, anti-TNF drugs, rituxan and other B-cell targeting agents, TNF-targeting agents, PD4 inhibitors, p38 inhibitors, PDE4 inhibitors, and antihistamines.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the zo particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 100 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician. In one embodiment, a compound of the invention may typically be administered at a dose from 0.1 mg/kg/day to 125 mg/kg/day. For example, a compound of the invention may be administered at a dosage of about 25 mg/kg/day, 50 mg/kg/day, 75 mg/kg/day, or 100 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, intrathecal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art.

All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, s preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

In addition to the formulations described above, for prolonged delivery, the compounds may also be formulated as a depot preparation for administration by, for example, as implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods and Uses

As shown herein, the small molecules administered to a patient in need thereof are useful in restoring physiology, as well as restore the transport of iron across monolayers in subject deficient in iron transporter.

Accordingly, the invention provides methods for the treatment or prevention of a disease, disorder, or condition associated with deficiency of or a defect in an iron transporter, comprising administering to a subject in need thereof a therapeutically effective amount of at least one small molecule, or with a pharmaceutical composition thereof.

In certain embodiments, the diseases, disorders, or conditions associated with a deficiency of or a defect in an iron transporter include hereditary hemochromatosis, iron deficiency anemia, hypochromic microcytic anemia, anemia of chronic disease; iron overload. In some embodiments, the diseases, disorders, or conditions associated with a deficiency of or a defect in an iron transporter include fatigue, lethargy; dizziness; headaches; shortness of breath; ringing in ears; taste disturbances; restless leg syndrome; pallor; flattened; brittle nails; angular stomatitis; glossitis; blue sclera pale conjunctivae; pica; decreased maximum aerobic capacity; decreased athletic performance; lowered endurance; impaired temperature regulation; and impaired cognitive functioning and memory.

In some aspects, the invention provides methods for increasing transepithelial iron transport in subject in need thereof, comprising administering to the subject a therapeutically effective amount of a small molecule, or a pharmaceutical composition thereof.

In some aspects, the invention of provides methods of increasing growth in in subject in need thereof, comprising administering to the subject a therapeutically effective amount of a small molecule, or a pharmaceutical composition thereof.

In some aspects, the invention of provides methods of increasing physiology in in subject in need thereof, comprising administering to the subject a therapeutically effective amount of a small molecule, or a pharmaceutical composition thereof.

In some aspects, the invention provides methods of increasing hemoglobinization in a patient in need thereof, comprising administering to the subject a therapeutically effective amount of a small molecule.

In some aspects, the invention provides methods of increasing iron release in a patient in need thereof, comprising administering to the subject a therapeutically effective amount of a small molecule.

In some aspects, the invention provides methods of increasing in vitro one or more of transepithelial iron transport, physiology or hemoglobinization in a cell.

In some aspects, the invention provides methods of increasing ex vivo one or more of transepithelial iron transport, physiology or hemoglobinization in a cell or organ.

Another aspect of the invention relates to methods of screening for a compound capable of treating a disease or condition characterized by a deficiency of or a defect in an iron transporter in a subject in need thereof, comprising the steps of:
 a) determining an increase in iron binding and transport;
 b) determining an increase in restoration of growth; and
 c) determining an increase in physiology in human disease-relevant system.

In certain embodiments, a small molecule identified by such a method is efficacious in treating a disease or condition characterized by a deficiency of or a defect in an iron transporter.

Alternatively, the efficacy of a small molecule for treating a disease or condition characterized by a deficiency of or a defect in an iron transporter can be determined via measuring iron binding transport, measuring restoration of growth, and measuring physiology in human disease-relevant system. In certain such embodiments, the binding transport, restoration of growth, and physiology in human disease-relevant system can be measured prior to and after administration of a small molecule. When the binding transport, restoration of growth, and physiology in human disease-relevant system increase after administration of a small molecule, such an agent is efficacious in treating a disease or condition characterized by a deficiency of or a defect in an iron transporter.

In some embodiments, the subject receiving treatment is a mammal. For instance, the methods and uses described herein are suitable for medical use in humans. Alternatively, the methods and uses are also suitable in a veterinary context, wherein the subject includes but is not limited to a rat, dog, cat, horse, cow, sheep and goat.

In some embodiments, the subject is deficient in an iron transporter. In some embodiments, the subject is deficient in transferrin receptor 1 (TFR1), or transferrin receptor 2 (TFR2). In some embodiments, the subject is deficient in divalent cation importers. In some embodiments, the subject is deficient in DMT1 or ZIP14 (Zrt-Irt-like protein 14). In some embodiments, the subject is deficient in FPN1. In some embodiments, the subject is deficient in Mitoferrin, TMPRSS6, frataxin, ceruloplasmin, Dcytb, FTH1, or HCP1.

EXAMPLES

Example 1. Identification of Small Molecules with the Capacity to Autonomously Transport Iron Across Lipid Bilayers.

To identify small molecules which perform such transport, a modified functional complementation experiment was performed. After screening small molecules thought to bind iron with growth-deficient S. cerevisiae missing the iron transporting complex Fet3Ftr1 (fet3Δftr1Δ), the natural product hinokitiol (FIG. 1, panel (E)) restored cell growth (FIG. 1, panels (F), (G)) independent of known siderophore transporters in yeast (FIG. 4, panel (A)). Growth rescue occurs under aerobic conditions (FIG. 4, panel (B)), suggesting intracellular iron utilization. Hinokitiol-treated fet3Δftr1Δ yeast grow to wild type levels (FIG. 1, panel (H)) with similar doubling times (FIG. 4, panel (C)). Growth restoration is not due to generic hormetic effects (FIG. 4, panel (D)) and can be sustained >40 days with continued reliance on hinokitiol (FIG. 4, panel (E)).

Example 2. Determination of Iron Binding and Transport.

Figure 4:
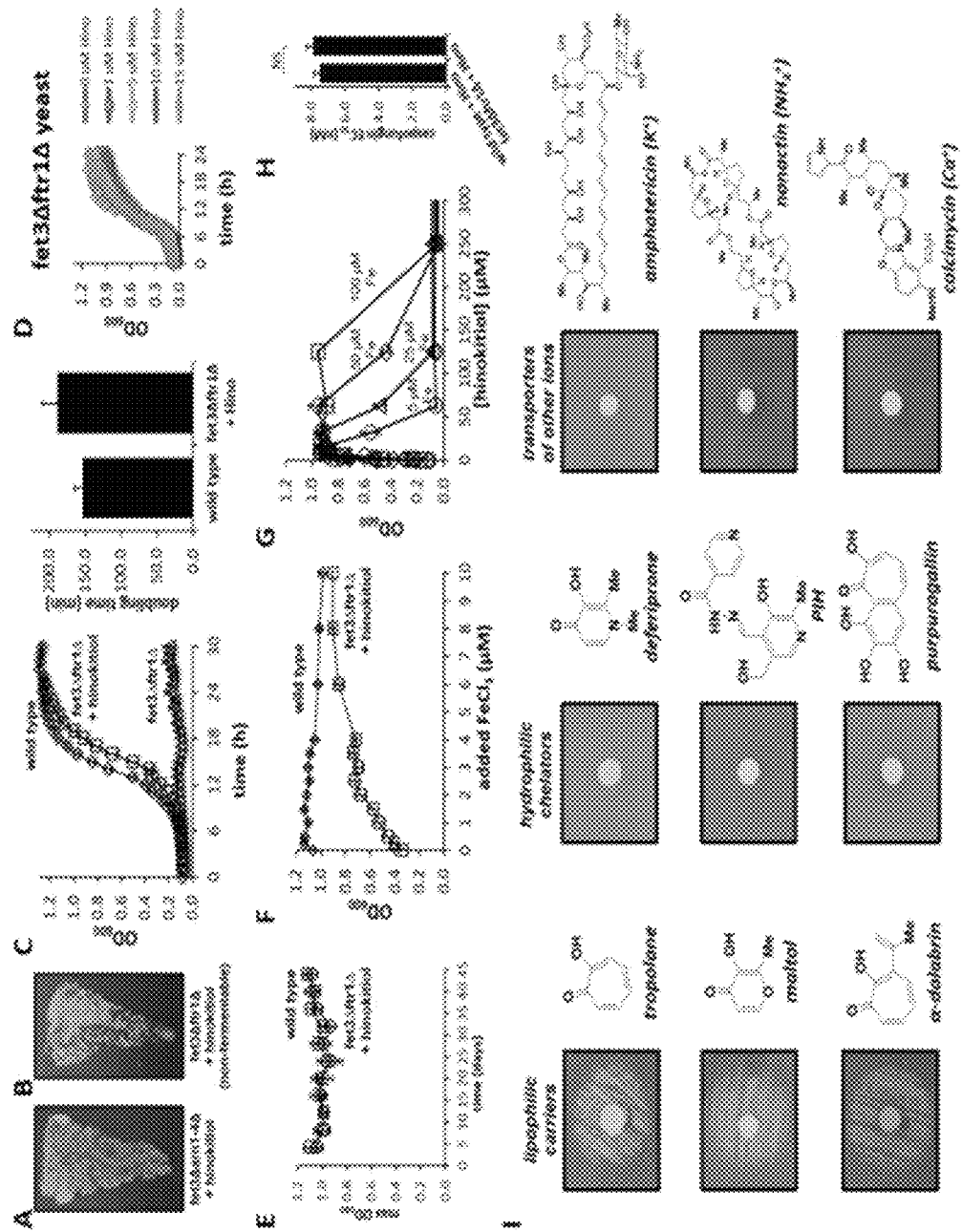
FIG. 4 illustrates that hinokitiol restores growth to iron transporter-deficient yeast. Panel (A) shows that hinokitiol growth restoration is independent of siderophore transporters in yeast; panel (B) shows that growth restoration occurs under aerobic conditions, indicating iron utilization under iron-strenuous conditions; panel (C) shows that hinokitiol restores growth to iron-deficient yeast with similar doubling times; panel (D) shows that restoration of growth is not due to hormetic effects; panel (E) shows that restoration of growth is sustainable with continued reliance on hinokitiol; panel (F) illustrates that the degree of hinokitiol-mediated restoration of growth is dependent on the amount of iron added to the media until it reaches normal levels; panel (G) shows that increasing the amount of iron increases the range of doses over which hinokitiol restores growth to yeast; panel (H) shows that hinokitiol-treated iron-deficient yeast are equi-sensitive to inhibition of an off-pathway inhibitor of cell wall biosynthesis (caspofungin); panel (I) shows that lipophilic iron carriers restore growth while hydrophilic ones do not. Transporters of other ions do not restore growth as well.
Figure 5:
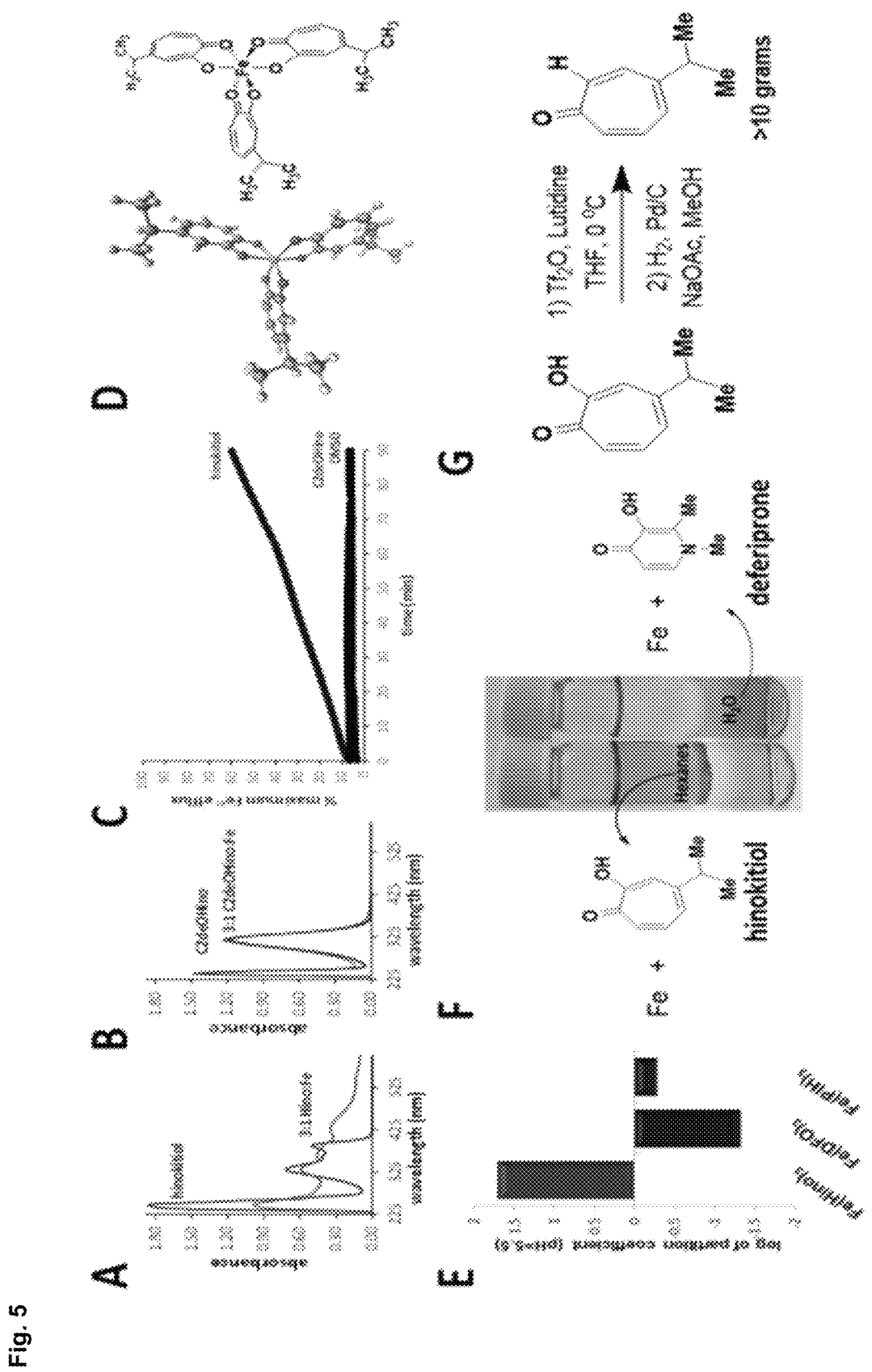
FIG. 5 illustrates the biophysical characterization of hinokitiol. Panel (A) represents a UV trace of hinokitiol after addition of iron supports it binds iron while C2deOHino does not, as illustrated in panel (B); panel (C) shows that hinokitiol promotes the release of iron from POPC liposomes while C2deOHino and DMSO vehicle do not; panel (D) shows that the X-ray crystal structure of hinokitiol suggests a hydrophobic exterior encasing a hydrophilic interior; panel (E) shows that a hinokitiol iron complex predominantly partitions into octanol, unlike water-soluble chelators (which do not rescue yeast growth); panel (F) shows that a hinokitiol iron complex is soluble in hexanes, whereas water-soluble chelators such as deferiprone partition primarily into water; panel (G) illustrates a multi-gram scale synthesis of C2deOHino.

To better understand the fundamental underpinnings behind hinokitiol-promoted restoration of fet3Δftr1Δ growth, iron binding and transport was confirmed (FIG. 5, panels (A), (C)). The crystal structure of a tris(hinacolato) iron (III) complex (FIG. 5, panel (D)) revealed a hydrophobic outer shell encasing a hydrophilic and iron binding central core. Opposite to water soluble iron chelators, which cannot rescue growth in this assay (FIG. 4, panel (I) and FIG. 4, panels (E), (F)), tris(hinacolato) iron (III) predominantly partitions into octanol (FIG. 4, panels (E), (F)). Synthetic deletion of the C-2 oxygen (FIG. 5, panel (G)) generating C2-deoxy hinokitiol (C2deOHino, FIG. 1, panel (E)) ablated iron binding and transport (FIG. 5, panels (B), (C)), making this a powerful probe for the role of iron transport in the biological activities of hinokitiol.

Example 3. Restoration of Physiology in Human Disease-Relevant Systems.

Hinokitiol's capacity to restore physiology in human disease-relevant systems was evaluated. DMT1-dependent non-heme iron absorption occurs in the microvilli of duodenal enterocytes before release to the blood and transferrin-mediated circulation. Transferrin-bound iron is then utilized peripherally after DMT1-mediated endosomal iron release to the cytosol and subsequent mitochondrial import in developing erythrons. DMT1 deficiencies lead to decreased iron absorption and reduced hemoglobinization in red blood cell progenitors collectively causing hypochromic, microcytic anemia. We hypothesized that hinokitiol could restore both iron absorption and intracellular iron transport, and as a result normal physiology, in DMT1-deficient models of nutrient absorption and erythroid maturation.

Hinokitiol-Promoted Transepithelial Iron Transport

Figure 2:
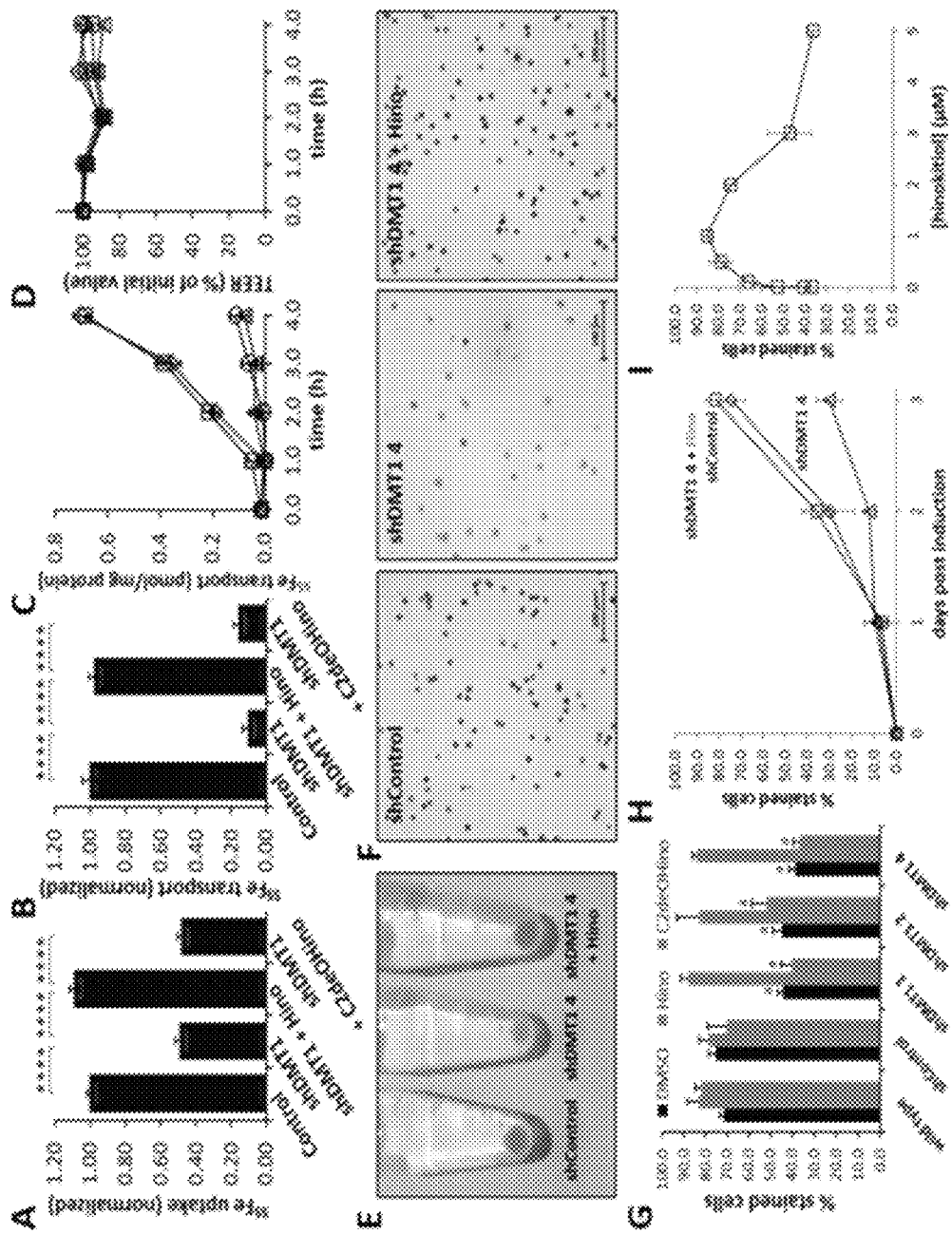
FIG. 2 illustrates that hinokitiol restores physiology in DMT1-deficiencies in vitro. Panel (A) shows that hinokitiol restores uptake into cells and Panel (B) shows that hinokitiol restores transepithelial transport in DMT1-deficient Caco-2 epithelia monolayers in a time-dependent (panel (C)) and dose-dependent manner (panel (D)). Panel (E) shows that hinokitiol restores differentiation in DMT1-deficient MEL cells as indicated by the presence of hemoglobin. Panel (F) represents the dianisidine staining of heme indicating that hinokitiol restores hemoglobinization which was quantified through Image J analysis (panel G). Panel (H) represents the time dependence hinokitiol-mediated rescue. Panel (I) shows that hinokitiol restores differentiation in a dose-dependent manner. Graphs depict mean±SEM.
Figure 6:
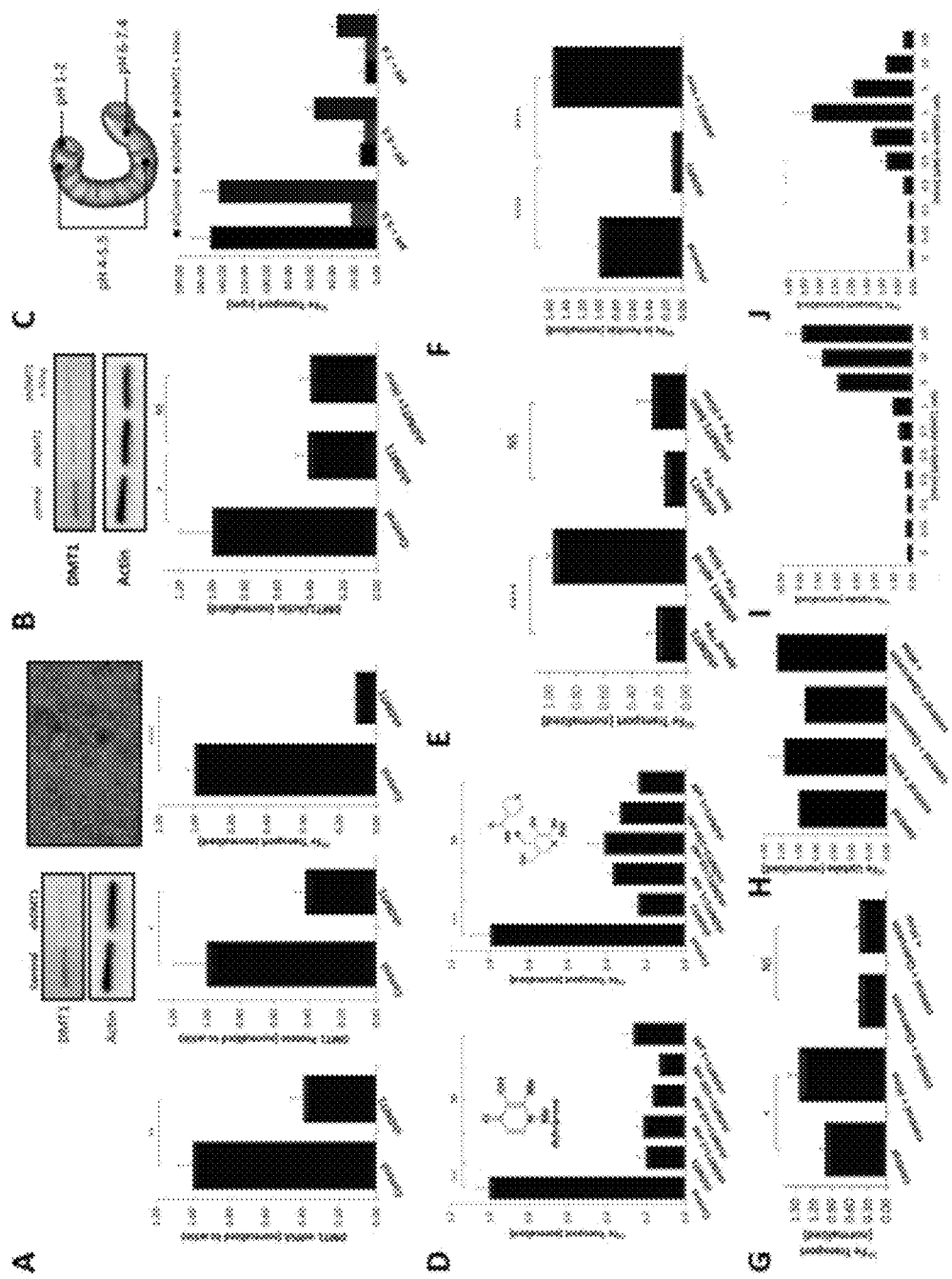
FIG. 6 illustrates that hinokitiol restores physiology to DMT1-deficient Caco-2 epithelia. Panel (A) shows that DMT1-knockdown Caco-2 cell lines were established through shRNA transfection; panel (B) shows that hinokitiol does not induce expression of DMT1; panel (C) illustrates that hinokitiol promotes transepithelial transport at a range of pH values found throughout the duodenum; panel (D) shows that water-soluble iron chelators do not promote iron transport; panel (E) shows that hinokitiol cannot promote similar basolateral to apical transport of iron; panel (F) shows that high iron incorporation into ferritin was observed after hinokitiol treatment and immunoprecipitation of ferritin; panel (G) shows that down-regulation of ferroportin 1 (FPN1) through quercetin ablated the capacity for hinokitiol to restore transport, and panel (H) shows that this is done without affecting uptake; panel (I) shows that uptake of iron into cells increases with increasing hinokitiol, however, panel (J) shows that transepithelial transport decreases at high concentrations of hinokitiol.

Hinokitiol-promoted transepithelial iron transport in differentiated Caco-2 gut epithelia monolayers was first evaluated. DMT1-deficient cells were established through stable shRNA transfection (FIG. 6, panel (A)). Using conditions commensurate with duodenal iron absorption, apical addition of $^{55}$Fe to control monolayers revealed both high $^{55}$Fe uptake into cells (FIG. 2, panel (A)) and transepithelial transport (FIG. 2, panel (B)) relative to shDMT1 monolayers. Both uptake and transport were restored (FIG. 2, panels (A), (B)) upon apical addition of hinokitiol (500 nM) at rates similar to those in controls (FIG. 2, panel (C)) without disrupting monolayer integrity (FIG. 2, panel (D)). Hinokitiol-mediated uptake and transport was independent of DMT1 expression (FIG. 6, panel (B)) and was maintained at a range of pHs observed throughout the duodenum (FIG. 6, panel (C)). C2deOHino was unable to promote uptake or transport (FIG. 2, panels (A), (B)), nor were water-soluble iron chelators deferiprone and pyridoxal isonicotinoyl hydrazone (FIG. 6, panel (D)).

Further studies revealed collaboration with the endogenous network of iron transporting proteins to achieve the observed restoration of transepithelial iron transport. Basolateral addition of $^{55}$Fe and hinokitiol failed to promote transport of iron from the basolateral to the apical side, inconsistent with small molecule only-mediated transepithelial iron transport (FIG. 6, panel (E)). In normal epithelia, iron brought into the cell via apical DMT1 transporters is stored in cytosolic ferritin clusters and directionally exported through the basolateral membrane by FPN1. Transepithelial iron flux via this network of proteins is regulated by the iron response element which is sensitive to intracellular iron concentrations. In control monolayers, immunoprecipitation of ferritin after apical addition of $^{55}$Fe revealed high iron incorporation, substantially reduced ferritin iron incorporation was observed in DMT1-deficient monolayers, and hinokitiol treatment restored high incorporation of $^{55}$Fe into ferritin (FIG. 6, panel (F)). Down-regulation of FPN1 expression in control monolayers with quercetin led to decreased transepithelial transport (FIG. 6, panel (G)) without affecting uptake (FIG. 6, panel (H)). Hinokitiol was unable to restore transepithelial transport in this system (FIG. 6, panel (G)), supporting the role of FPN1 in hinokitiol-mediated restoration of transport. Finally, $^{55}$Fe uptake into DMT1-deficient monolayers was proportional to the hinokitiol dosage (FIG. 6, panel (I)), but transepithelial $^{55}$Fe transport was reduced when a high intracellular iron concentration is reached (FIG. 6, panel (J)). Collectively, this data suggests hinokitiol-mediated transepithelial iron transport may be regulated by the endogenous iron response element controlled pathway.

Example 4. Restoration of Hemoglobinization in DMT1-Deficient Erythroid Progenitors.

The capacity for hinokitiol to restore hemoglobinization in DMT1-deficient erythroid progenitors was evaluated. Reticulocytes isolated ex vivo from DMT1-deficient Belgrade (b/b) and healthy (+/b) rats were incubated in plasma spiked with $^{59}$Fe-transferrin to assess hinokitiol's ability to promote iron utilization. Hinokitiol increased $^{59}$Fe incorporation into heme in a dose-dependent fashion (FIG. 7, panel (A)) at concentrations that did not cause hemolysis, while C2deOHino had no apparent effect.

Figure 7:
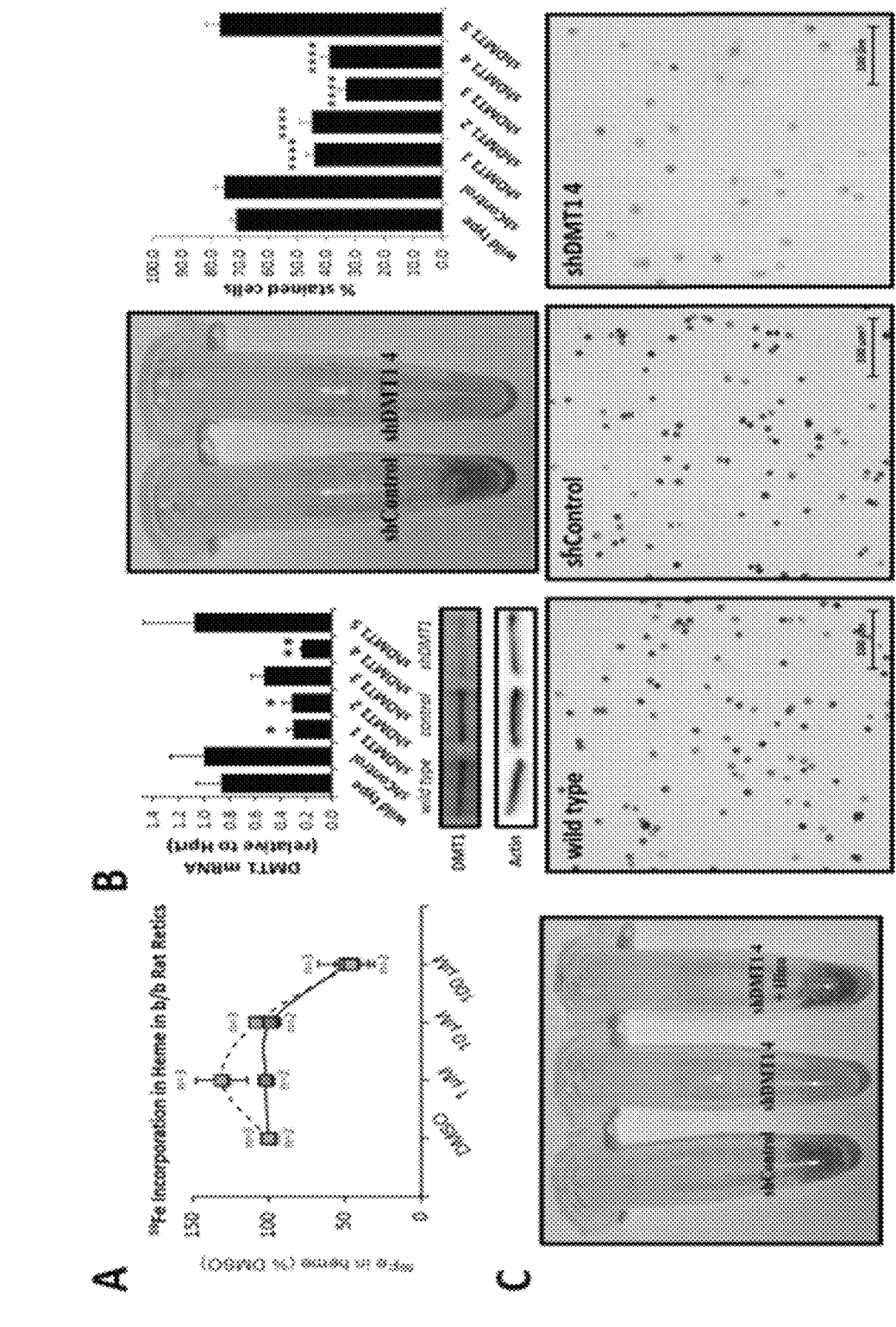
FIG. 7 illustrates that hinokitiol restores physiology to DMT1-deficient erythrocyte progenitors. Panel (A) illustrates that hinokitiol increases incorporation into heme for DMT1-deficient reticulocytes isolated from b/b rats ex vivo; panel (B) shows the development of DMT1-deficient MEL cells through shRNA transfection; and panel (C) shows that hinokitiol restores hemoglobinization to DMT1-deficient MEL cells similar to control cells as indicated by brown staining with o-dianisidine.
Figure 8:
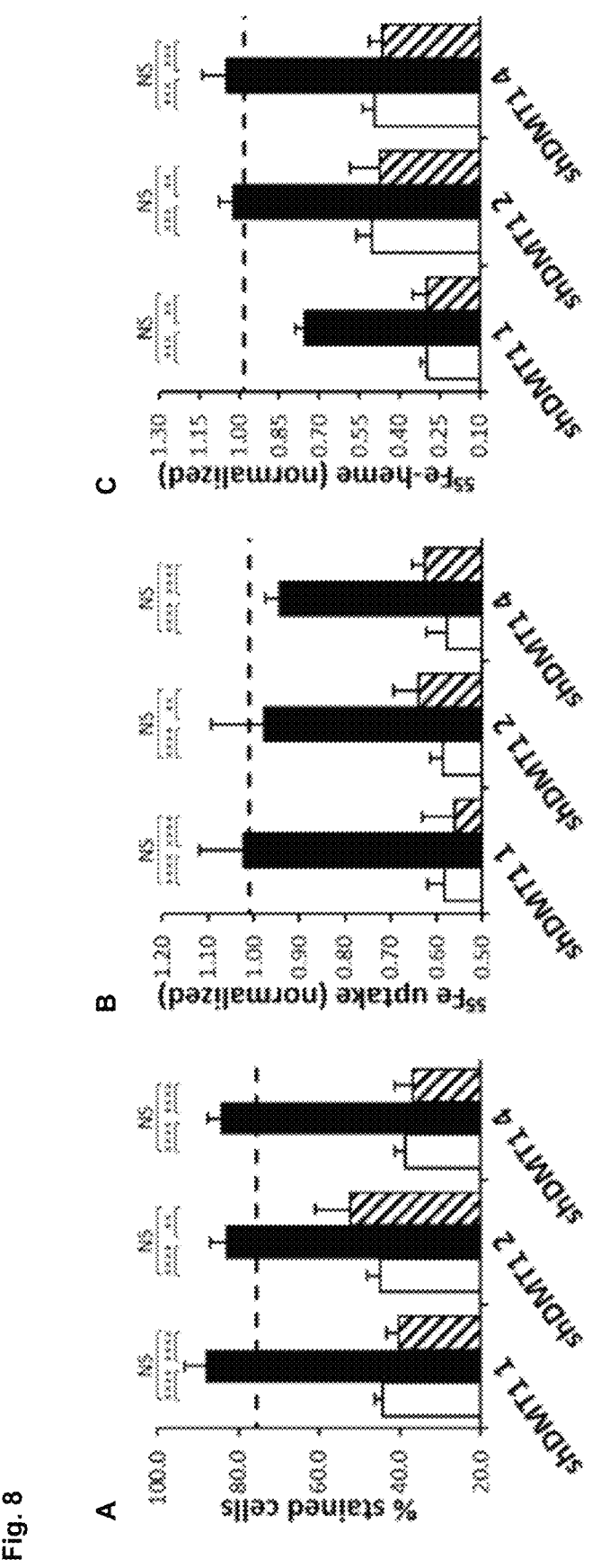
FIG. 8 is a series of bar graphs depicting that hinokitiol restores physiology in DMT1-deficient MEL cells in vitro. Panel (A) depicts iron staining; panel (B) depicts $^{55}$Fe uptake; and panel (C) depicts $^{55}$Fe-heme incorporation.

To gain a better fundamental understanding of this phenomenon, DS19 murine erythroleukemia (MEL) cells were used. These terminally differentiate toward developing erythrocytes after induction with 2% DMSO leading to increased iron uptake and globin expression. DMT1-deficient cell lines through shRNA knockdown were developed (FIG. 7, panel (B)). These cells exhibited reduced DMT1 mRNA, protein levels, and decreased rates of differentiation. Control cells differentiated normally as indicated by significant staining of hemoglobinized cells relative to shDMT1 cells (FIG. 2, panels (E)-(G) and FIG. 7, panel (C)). Addition of hinokitiol followed by incubation for 72 hours restored differentiation to these cells, as determined by positive staining of hemoglobinized cells with o-dianisidine (FIG. 2, panels (E)-(G); FIG. 7, panel (C); and FIG. 8, panel (A)), without toxicity in a time—(FIG. 2, panel (H)) and dose-dependent (FIG. 2, panel (I)) fashion. Restored differentiation was further evidenced by quantification of $^{55}$Fe uptake into these cells (FIG. 8, panel (B)), and $^{55}$Fe incorporation into heme (FIG. 8, panel (C)). Importantly, hinokitiol was unable to promote differentiation without DMSO induction. C2deOHino was unable to restore physiology in any case (FIG. 2, panel (G)).

Figure 9:
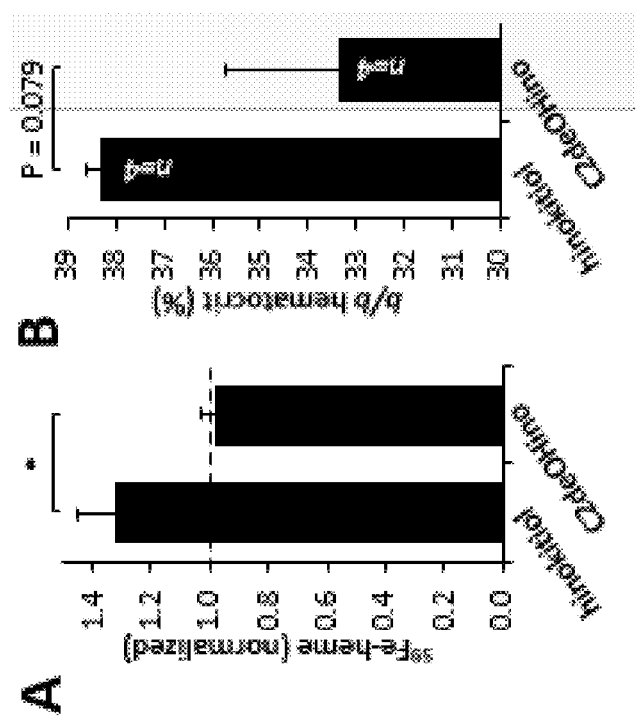
FIG. 9 is a pair of bar graphs depicting that hinokitiol restores physiology in DMT1-deficient Belgrade (b/b) rats. Panel (A) depicts hemoglobinization in isolated b/b reticulocytes; and panel (B) depicts the in vivo effect on hematocrit of chronic exposure of b/b rats to hinokitiol or C2deOHinokitiol.
Figure 10:
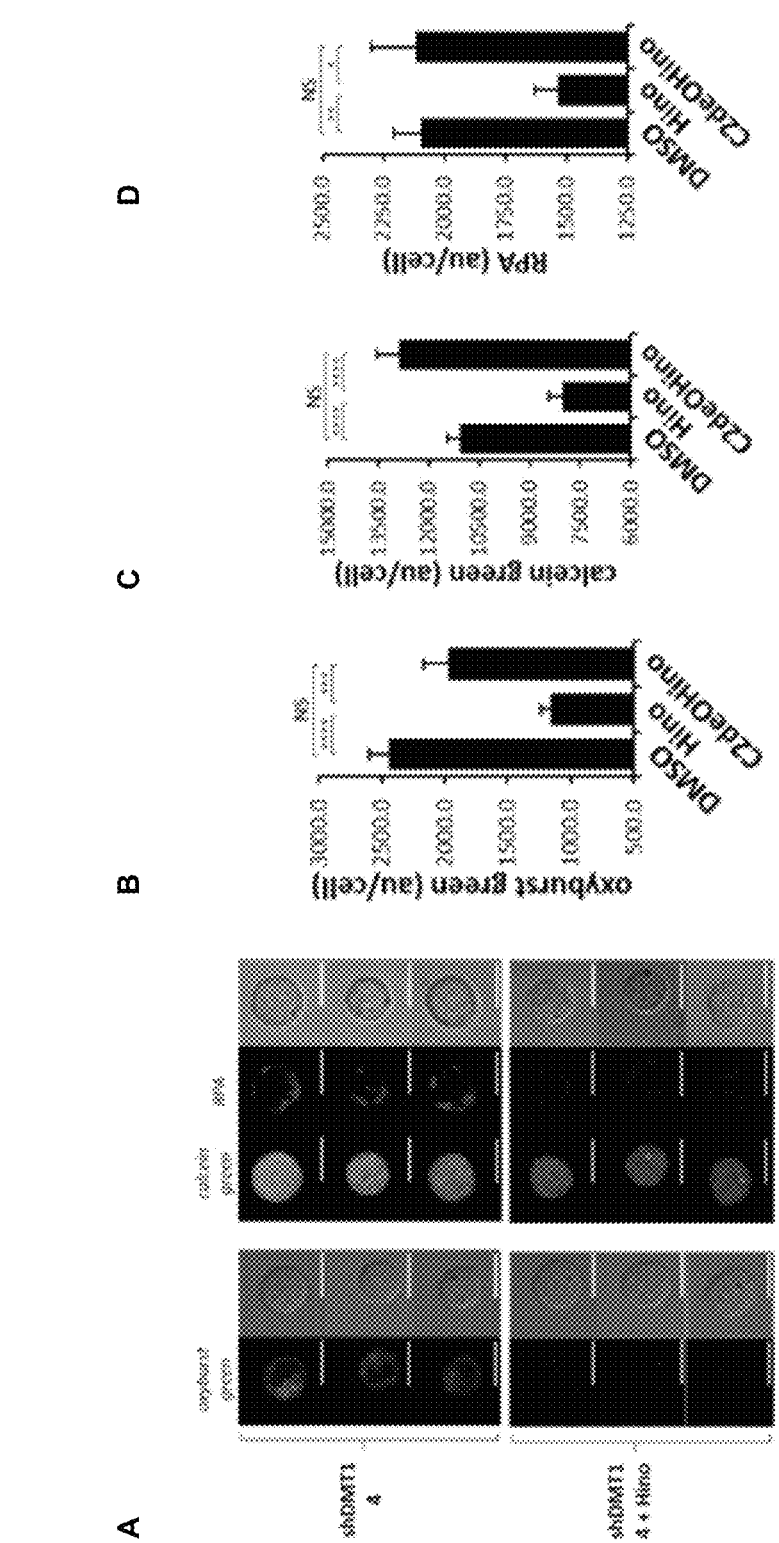
FIG. 10 illustrates that hinokitiol promotes the release of iron from endosomes into the cytosol, and subsequent mitochondrial uptake. Panel (A) depicts live cell fluorescence imaging with iron-specific dyes oxyburst green, calcein green, and RPA; panel (B) depicts quantified results for oxyburst green, indicating endosomes; panel (C) depicts quantified results for calcein green, indicating cytosol; and panel (D) depicts quantified results for RPA, indicating mitochondria.
Figure 11:
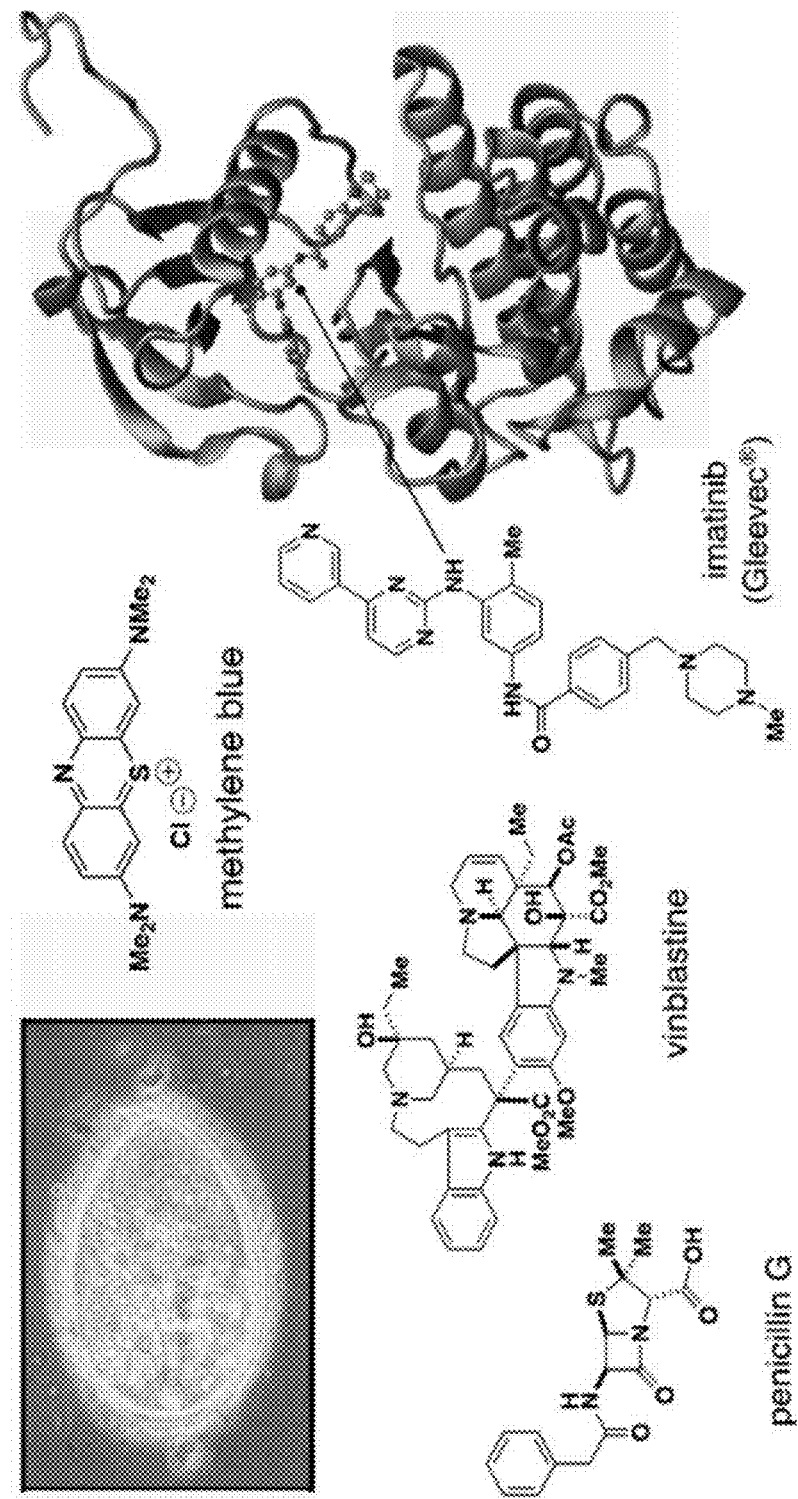
FIG. 11 represents the effect of small molecule inhibitors on excess protein function.
Figure 12:
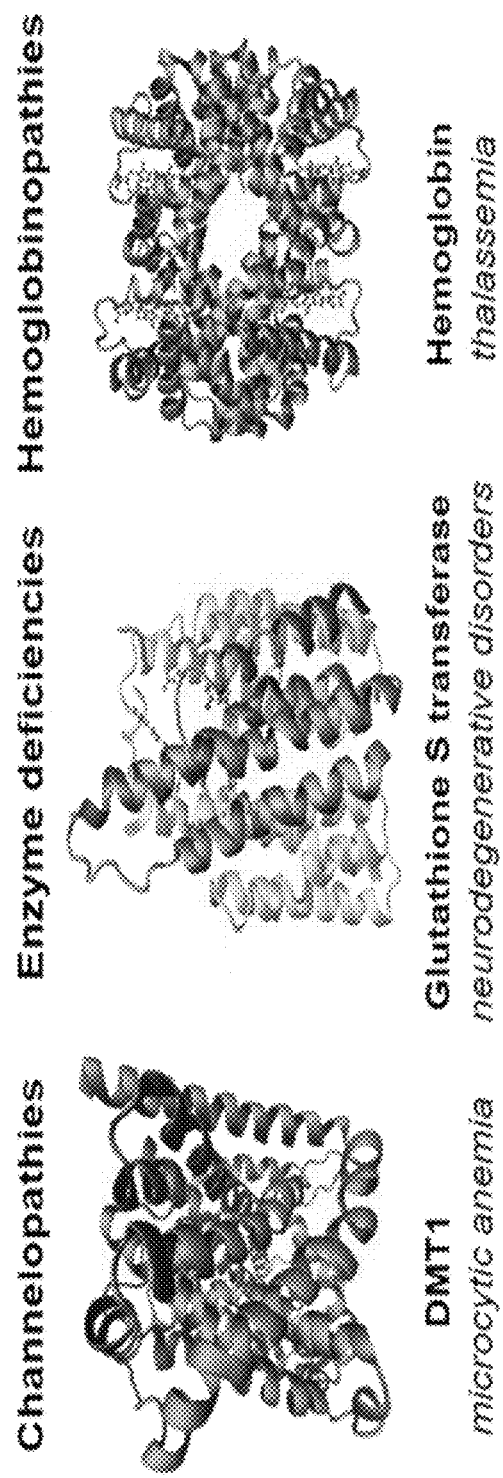
FIG. 12 illustrates the prospect of molecular prosthetics in the deficiency of protein function.
Figure 13:
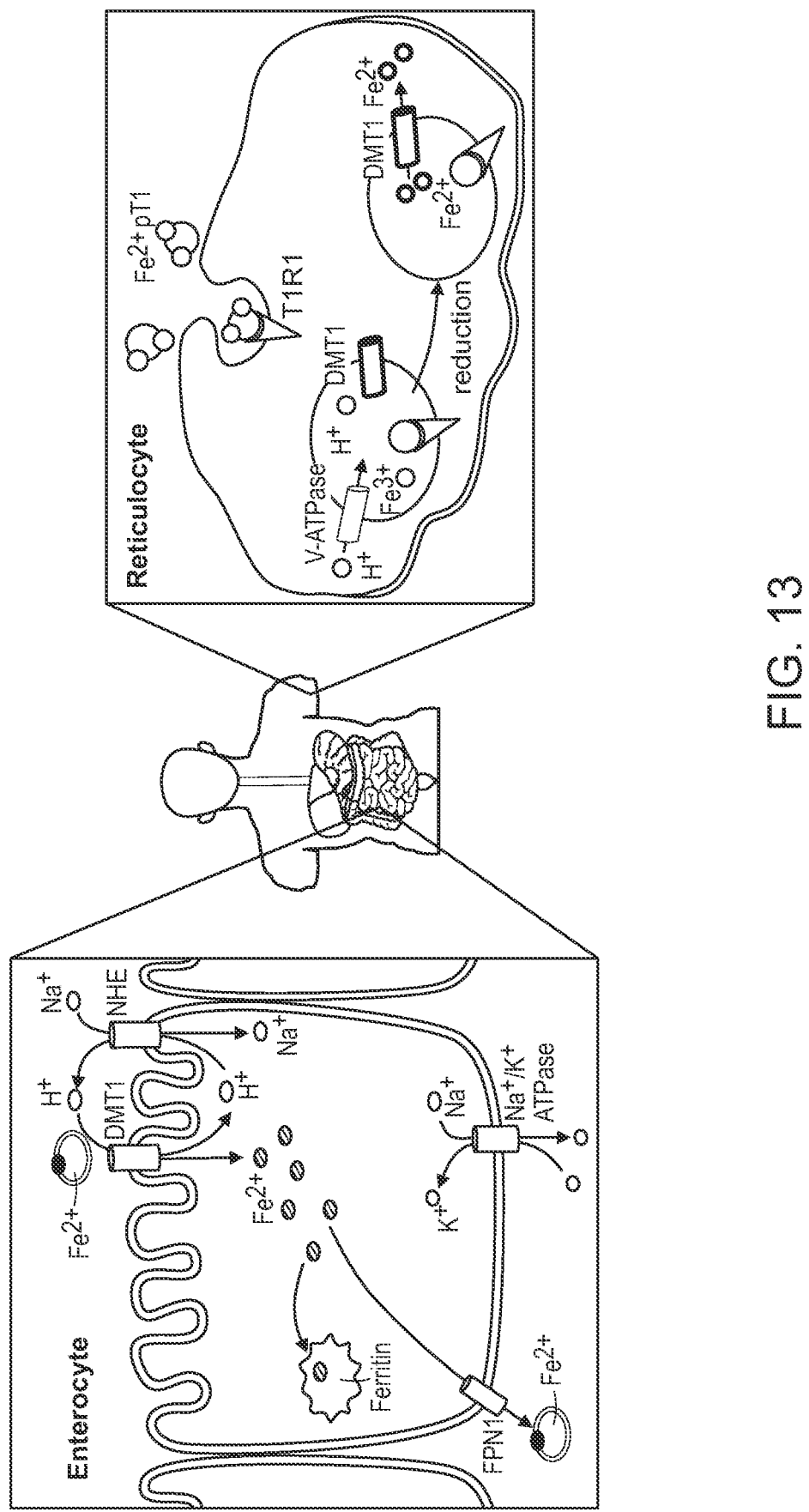
FIG. 13 illustrates deficiencies of DMT1 leading to hypochromic, microcytic anemia.
Figure 14:
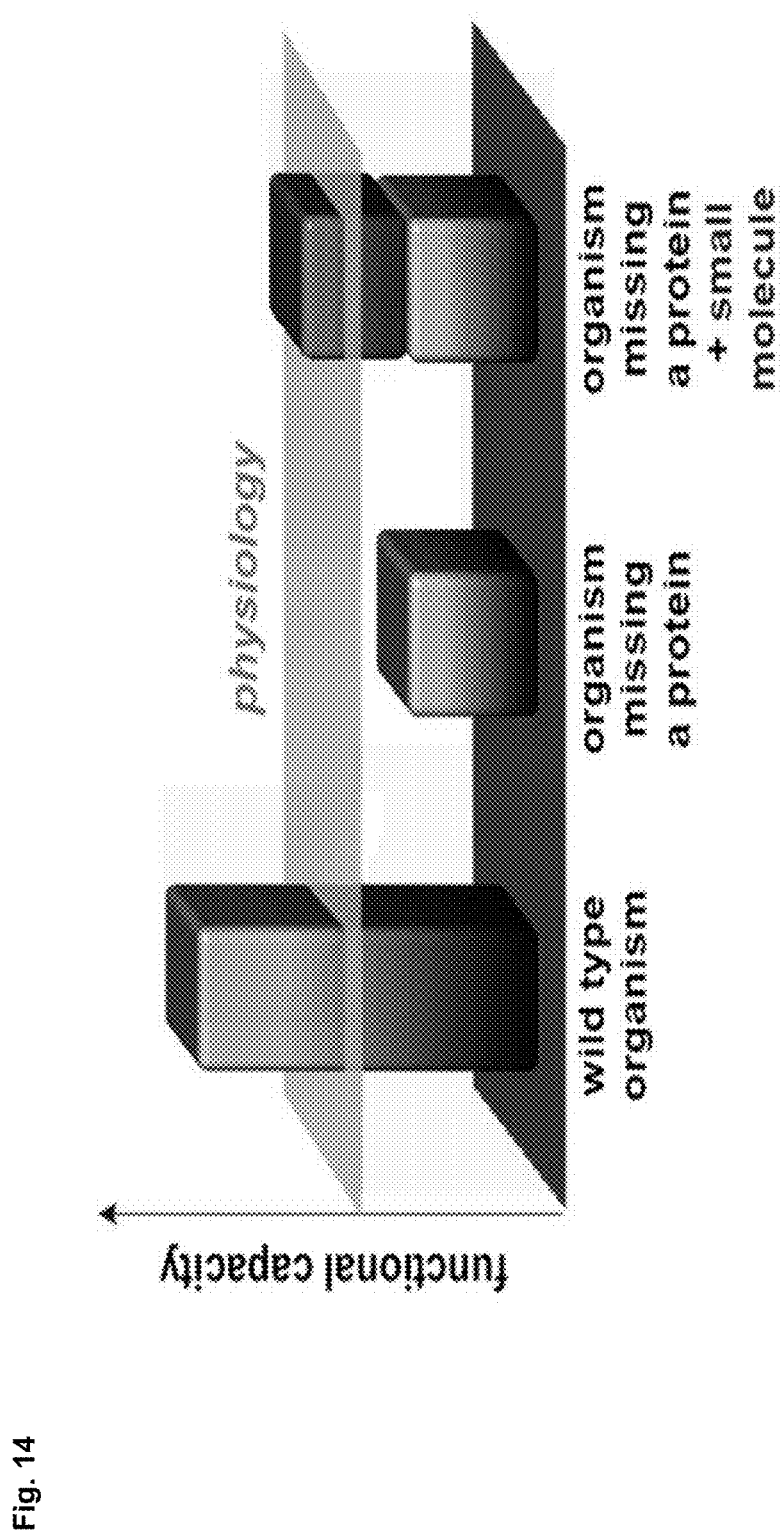
FIG. 14 illustrates the robustness hypothesis.
Figure 15:
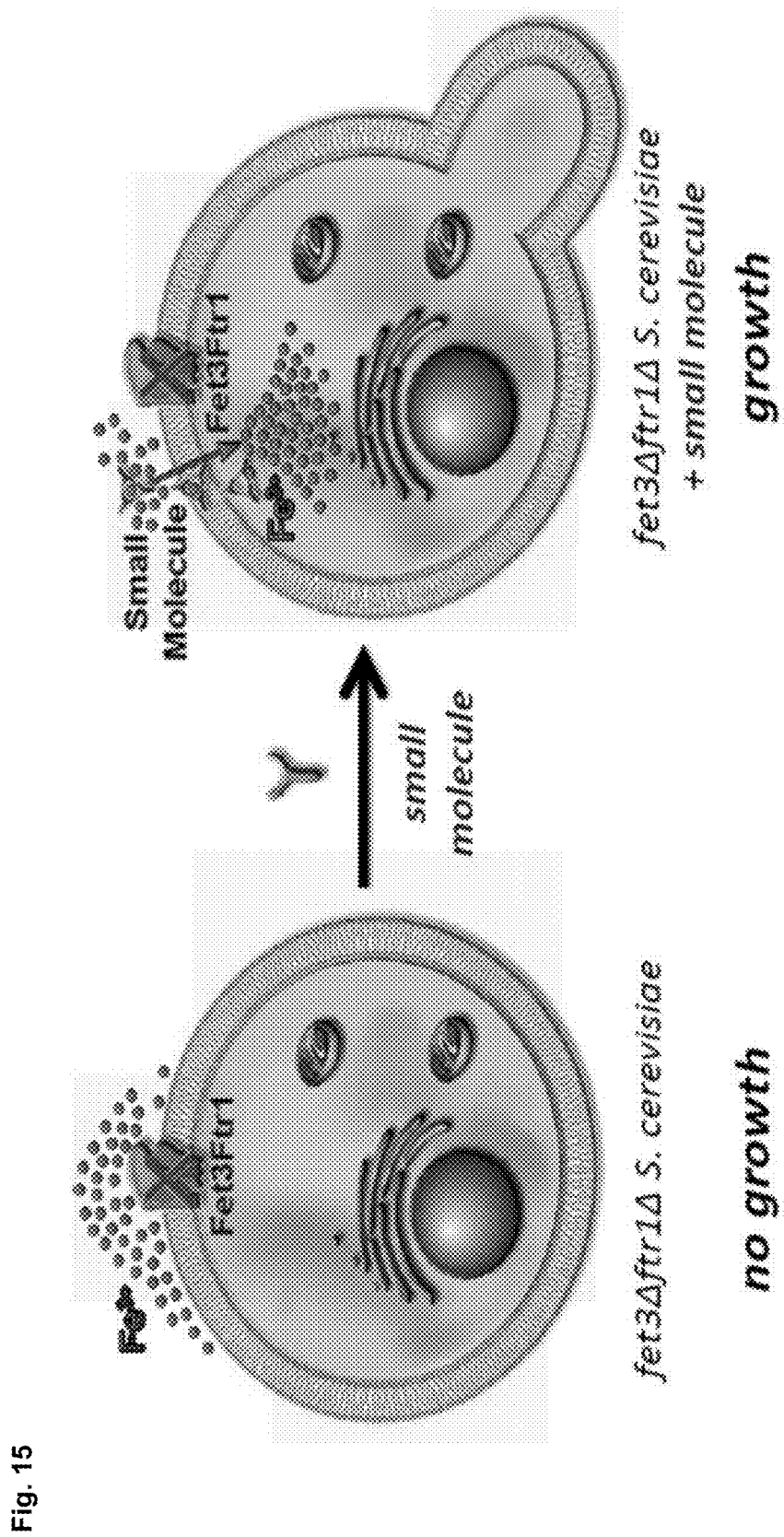
FIG. 15 represents small molecule functional complementation.
Figure 16:
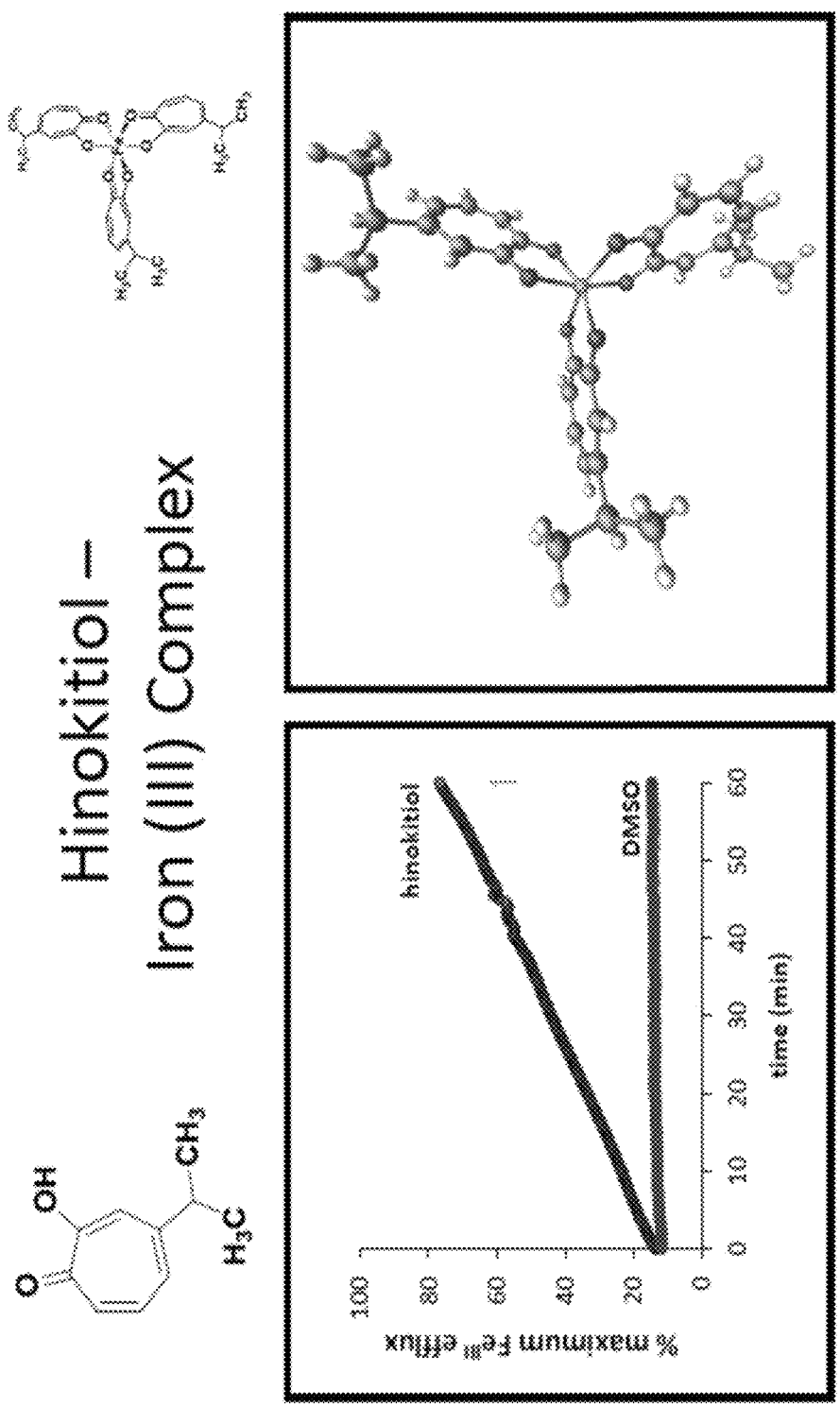
FIG. 16 illustrates that hinokitiol autonomously transports iron.
Figure 17:
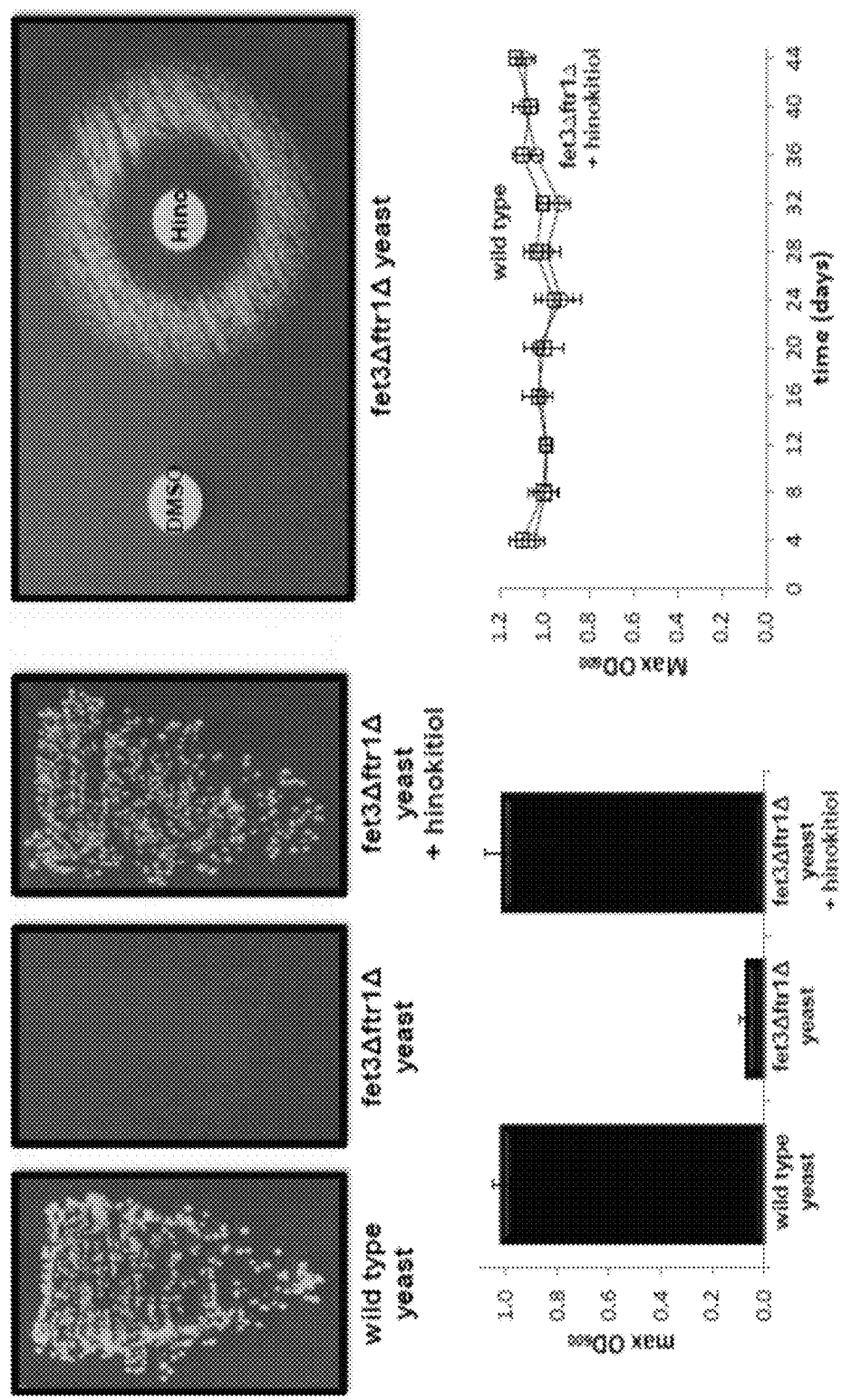
FIG. 17 illustrates that hinokitiol restores physiology in yeast.
Figure 18:
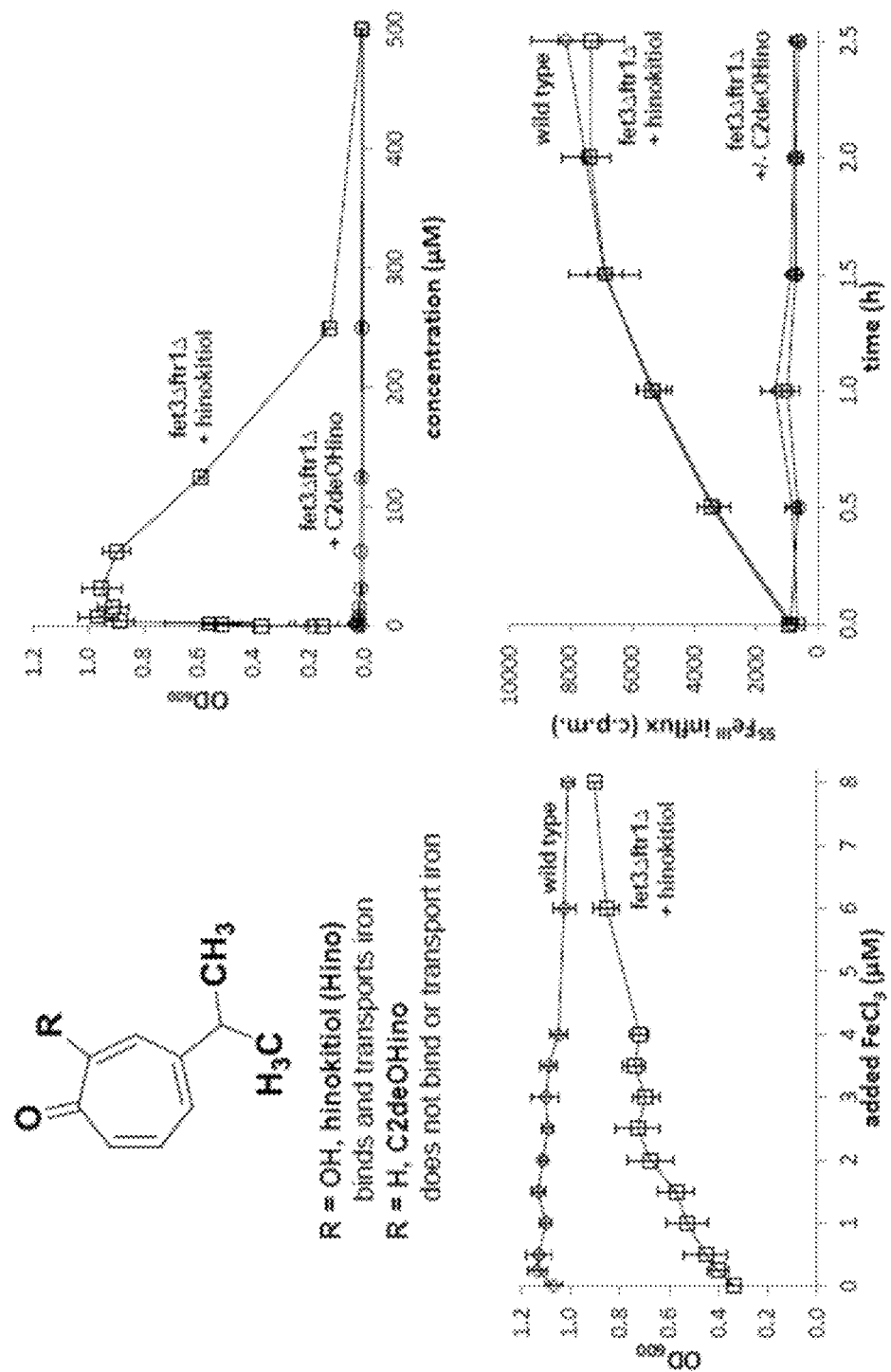
FIG. 18 illustrates that growth is dependent on iron transport.
Figure 19:
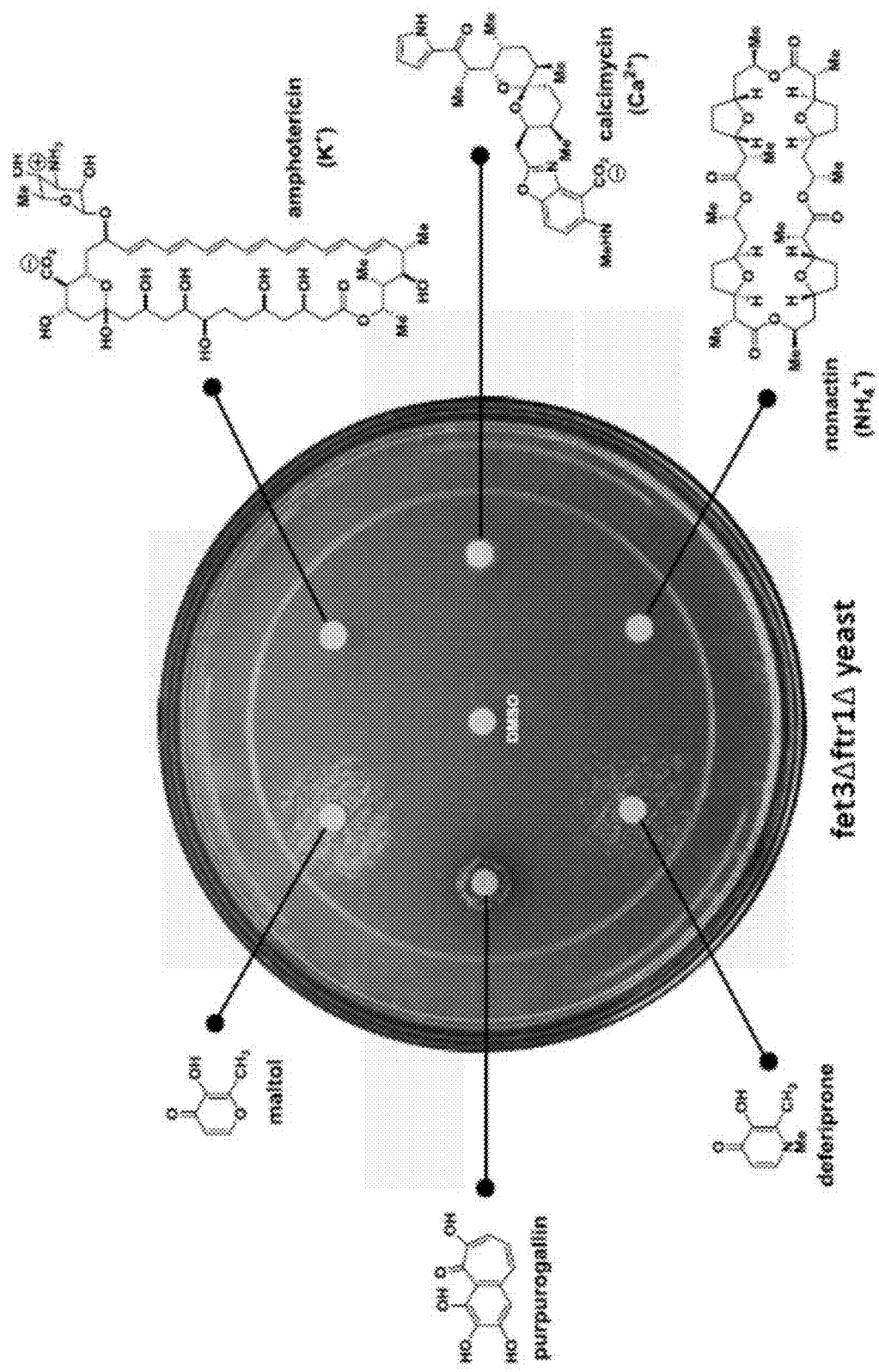
FIG. 19 shows functional complementation for a number of small molecules.
Figure 20:
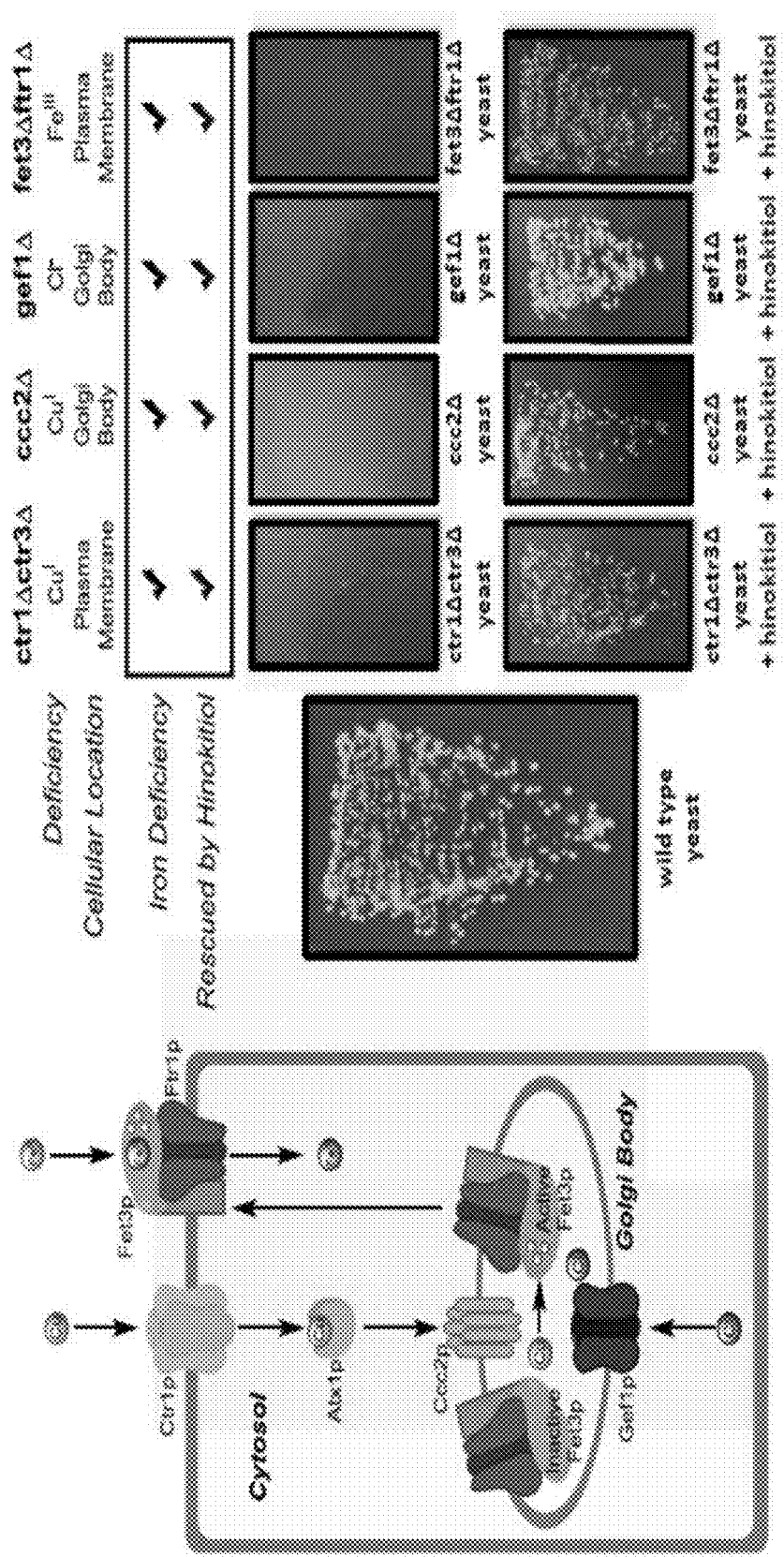
FIG. 20 shows downstream restoration of physiology.
Figure 21:
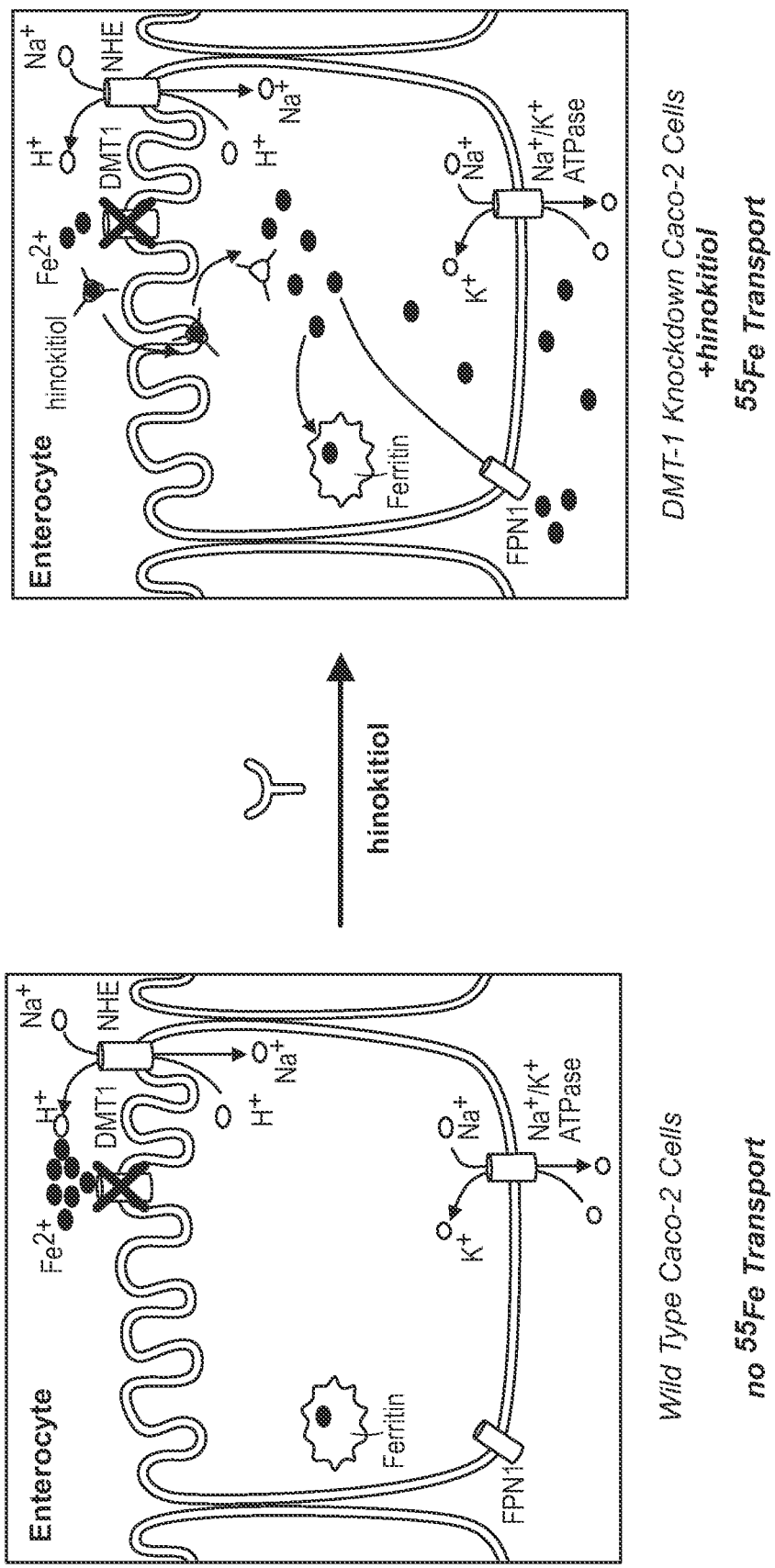
FIG. 21 illustrates replacing function in gut epithelia tissue.
Figure 22:
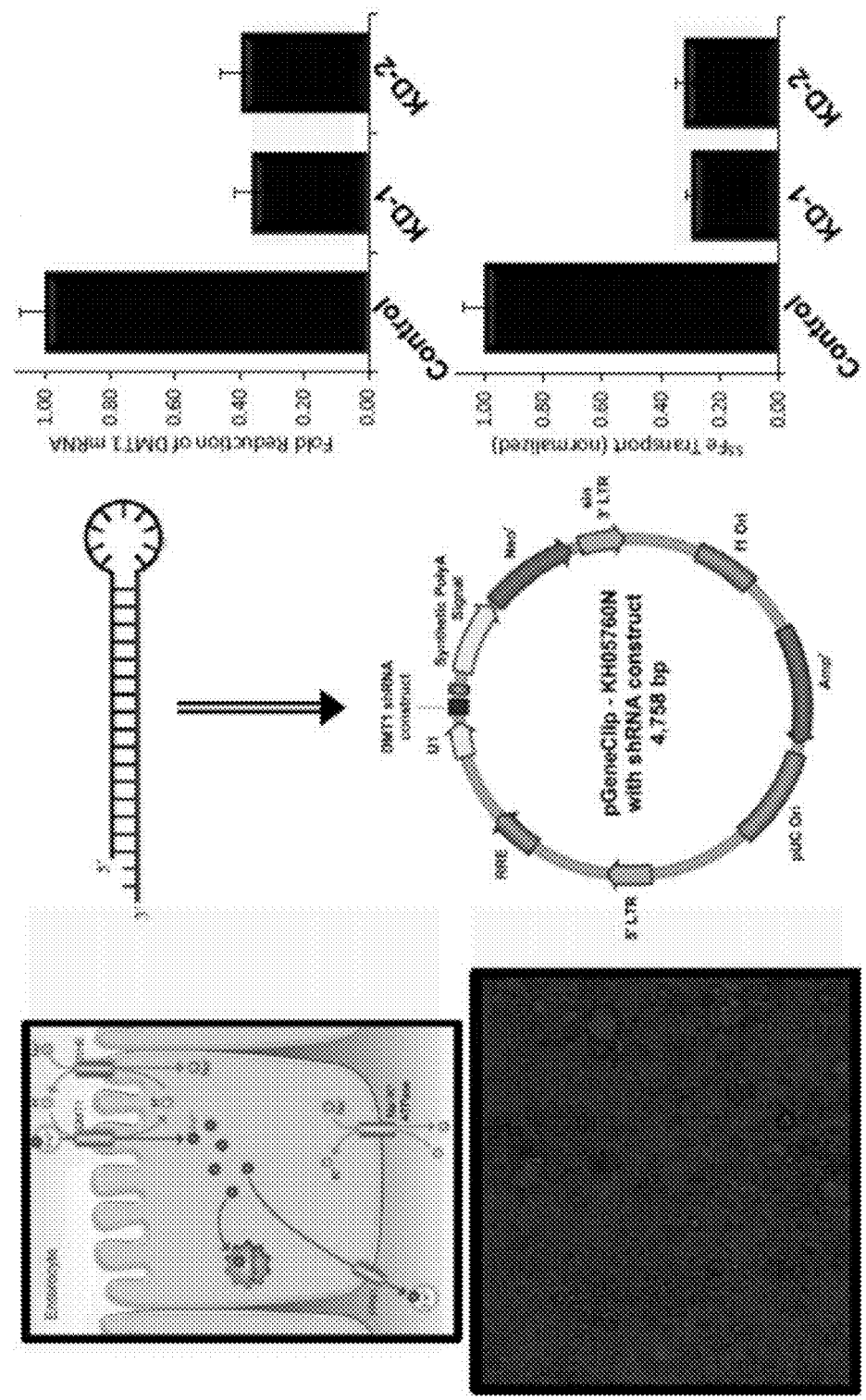
FIG. 22 shows functional complementation in monolayers of human enterocytes.
Figure 23:
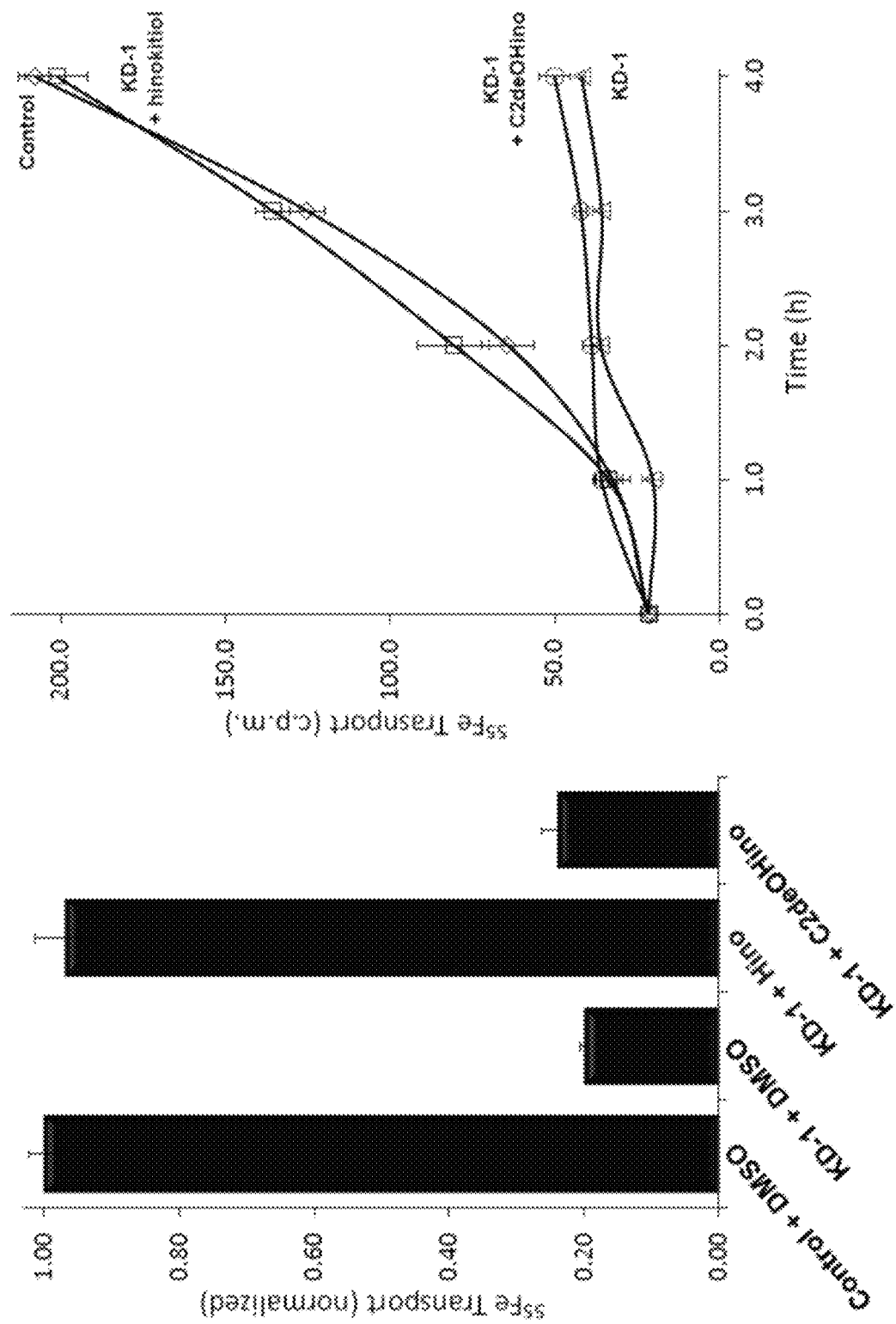
FIG. 23 illustrates that hinokitiol permeabilizes Caco-2 cells.

Furthermore, hinokitiol restored incorporation of $^{59}$Fe into heme in reticulocytes isolated from DMT1-deficient Belgrade (b/b) rats ex vivo (FIG. 9, panel (A)). The use of these MEL cells allowed us to test the hypothesis that hinokitiol autonomously transports iron down pre-existing concentration gradients. To do this, we utilized live cell fluorescence imaging with iron-specific dyes to visualize intracellular iron distribution. Specifically, the use of oxyburst green (FIG. 10, panels (A),(B)) showed high levels of iron in endosomes of DMT1-deficient cells as indicated by high intensity fluorescence, consistent with the role of DMT1 releasing iron from the endosome into the cytosol. Further, we observed relatively low levels of cytosolic iron (FIG. 10, panels (A),(C)) and mitochondrial iron (FIG. 10, panels (A),(D)), as indicated by minimal quenching of calcein green and RPA, respectively. Strikingly, addition of hinokitiol decreased endosomal iron levels and increased cytosolic and mitochondrial levels, consistent with releasing iron across the lipid membranes that normally host DMT1 (FIG. 10, panels (A)-(D)).

Example 5. Restoration of Physiology in DMT1-Deficient Animals.

Figure 3:
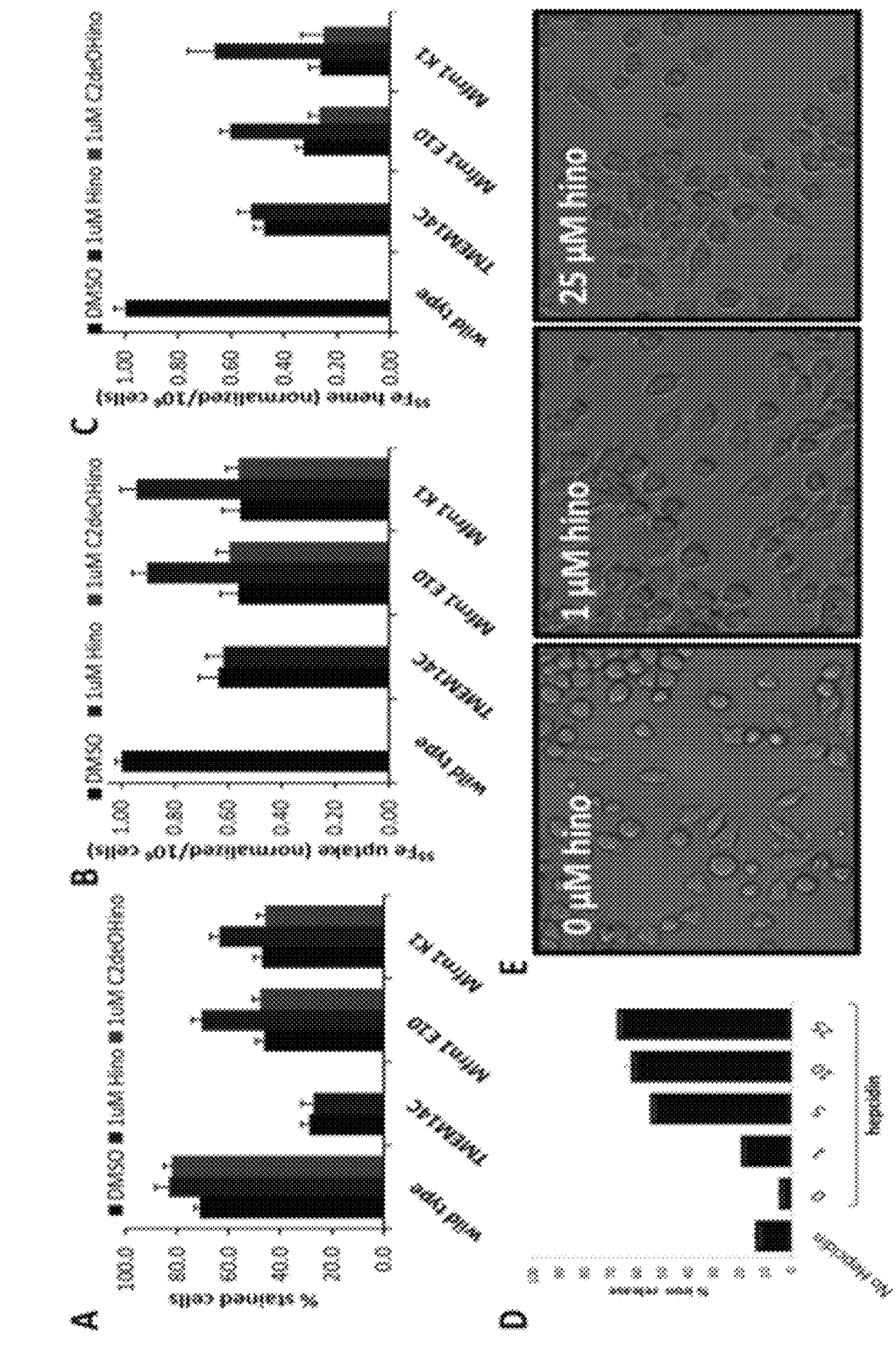
FIG. 3 shows that hinokitiol restores physiology in DMT1-deficiencies in vivo. Panel (A) represents Belgrade (b/b) rats exhibiting severe anemia; panel (B) illustrates hinokitiol's half-life determination after IP injection in F344 rats; panel (C) shows that hinokitiol in rat chow restores hematocrit to non-anemic values in b/b rats after 1 month of treatment at ~100 mg/kg; panel (D) shows that FPN1 was thus down-regulated with hepcidin leading to reduced iron release panel (E) shows that addition of hinokitiol released this intracellular iron back to normal levels in dose-dependent fashion without observable toxicity.

After observing the capacity for hinokitiol to restore iron absorption and hemoglobinization in vitro, hinokitiol was evaluated for restoration of physiology in DMT1-deficient animals. Belgrade (b/b) rats (FIG. 3, panel (A)) are the leading model of the disease and display severe hematological defects such as decreased hematocrit values amongst other markers. Hinokitiol was relatively non-toxic in healthy rats with reasonable pharmacokinetic half life (FIG. 3, panel (B)), and permeability assays suggested good oral bioavailability in vivo. Chronic exposure of b/b rats to hinokitiol and C2deOHino, a derivative that does not bind or transport iron, in rat chow (0.2% of feed) was performed. This hinokitiol dosage has previously been shown to be non-lethal after 13 weeks of treatment orally (Y. M. Cho et al., A 13-week subchronic toxicity study of hinokitiol administered in the diet to F344 rats. *Food Chem Toxocol* 49, 1782-1786 (2011)), and came to ~125 mg/kg treatments each day. After four weeks of treatment, significant increases in hematocrit were observed and exceeded values indicative of a non-anemic state (FIG. 3, panel (C)). Strikingly, after one month of treatment, 0.2% hinokitiol (~100 mg/kg/day) restored hematocrit to b/b rats to levels that are no longer considered anemic (FIG. 9, panel (B)), while C2deOHino gave low hematocrits normally observed for untreated b/b rats. This was sustained for >2 months.

Example 6. Restoring Physiology in Disease Models.

Hinokitiol was evaluated to restore physiology in disease models of other iron transporter deficiencies. Many mitochondriopathies lead to impaired iron utilization resulting in anemia. For example, a deficiency of mitoferrin, found on the inner mitochondrial membrane, leads to decreased iron import into the mitochondrial matrix. This reduces hemoglobin levels causing hypochromic anemia. Hinokitiol was thus tested for treating this alternative cause of anemia.

Mitoferrin-deficient MEL cell lines were established through CRISPR/Cas9-mediated knockout and exhibited reduced hemoglobinization (FIG. 4, panel (A)). Under identical conditions used to restore hemoglobinization to DMT1-deficient cells, hinokitiol restored hemoglobinization (FIG. 4, panel (A)). This was further supported by increases in $^{55}$Fe uptake and incorporation into heme (FIG. 4, panels (B), (C)). C2deOHino did not produce these effects (FIG. 4, panels (A)-(C)). As further evidence for the role of hinokitiol-promoted iron transport in restoring normal hemoglobinization, genetic deficiencies of enzymes involved in heme biosynthesis (TMEM14CΔ) were used. Hinokitiol treatment did not restore hemoglobinization (FIG. 4, panels (A)-(C)).

Example 7. Promoting Iron Release from FPN1-Deficient Systems.

Hemochromatosis is the leading hereditary disease in the U.S., and can be caused by deficiencies of FPN1. FPN1 is the main exporter of iron from enterocytes into the blood, and it further plays a role in releasing iron from liver reticuloendothelial macrophages after erythrophagocytosis of senescent red blood cells. Observing the striking generality of hinokitiol-promoted iron absorption and intracellular re-distribution, hinokitiol was additionally evaluated to promote iron release from FPN1-deficient systems.

To test the capacity for hinokitiol to restore iron release in FPN1 deficiencies, J774 macrophages were utilized. J774 cells with $^{55}$Fe-transferrin were incubated in the absence or presence of hepcidin. Hepcidin is a key iron regulator, down-regulating FPN1 by promoting its degradation. FPN1 was thus down-regulated with hepcidin leading to reduced iron release (FIG. 3, panel (D)). Addition of hinokitiol released this intracellular iron back to normal levels in dose-dependent fashion (FIG. 3, panel (D)) without observable toxicity (FIG. 3, panel (E)).

Collectively, the results establish that a small molecule autonomously performing protein-like function is able to generally restore physiology in vitro and in significantly more complex multi-cellular organisms in vivo.

We claim:

1. A method of treating a disease or condition characterized by a deficiency of or a defect in an iron transporter, comprising administering to a subject in need thereof a therapeutically effective amount of a small molecule, thereby treating the disease or condition;
wherein:
the disease or condition characterized by a deficiency of or defect in an iron transporter is selected from the group consisting of hypochromic, microcytic anemia, iron deficiency anemia, and a disease or disorder characterized by a deficiency in divalent metal transporter 1 (DMT1);
the small molecule is hinokitiol; and
the subject is a mammal.

2. The method of claim 1, wherein the small molecule is administered systemically, orally or intravenously.

3. The method of claim 1, wherein the subject is a human.

4. The method of claim 1, wherein the disease or condition characterized by a deficiency of or defect in an iron transporter is selected from the group consisting of hypochromic, microcytic anemia, iron deficiency anemia, and a disease or disorder characterized by a deficiency in divalent metal transporter 1 (DMT1).

5. The method of claim 2, wherein the subject is a human.

6. The method of claim 4, wherein the subject is a human.

7. The method of claim 6, wherein the small molecule is administered systemically, orally or intravenously.

8. The method of claim 1, wherein the disease or condition characterized by a deficiency of or defect in an iron transporter is iron deficiency anemia.

9. The method of claim 1, wherein the disease or condition characterized by a deficiency of or defect in an iron transporter is hypochromic microcytic anemia.

10. The method of claim 3, wherein the disease or condition characterized by a deficiency of or defect in an iron transporter is iron deficiency anemia.

11. The method of claim 3, wherein the disease or condition characterized by a deficiency of or defect in an iron transporter is hypochromic microcytic anemia.

12. The method of claim 5, wherein the disease or condition characterized by a deficiency of or defect in an iron transporter is iron deficiency anemia.

13. The method of claim 5, wherein the disease or condition characterized by a deficiency of or defect in an iron transporter is hypochromic microcytic anemia.

14. The method of claim 6, wherein the disease or condition characterized by a deficiency of or defect in an iron transporter is iron deficiency anemia.

15. The method of claim 6, wherein the disease or condition characterized by a deficiency of or defect in an iron transporter is hypochromic microcytic anemia.

\* \* \* \* \*